(12) United States Patent
Gooch et al.

(10) Patent No.: US 10,226,047 B2
(45) Date of Patent: *Mar. 12, 2019

(54) FIBROUS ANTIMICROBIAL MATERIALS, STRUCTURES, AND BARRIER APPLICATIONS

(71) Applicant: HydroAir Global, LLC, Lawrenceville, GA (US)

(72) Inventors: Jan W. Gooch, Atlanta, GA (US); Thomas J. Steimer, Sr., Athens, GA (US)

(73) Assignee: HYDROAIR GLOBAL, LLC, Lawrenceville, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/580,733

(22) Filed: Dec. 23, 2014

(65) Prior Publication Data

US 2015/0110843 A1    Apr. 23, 2015

Related U.S. Application Data

(63) Continuation of application No. 12/904,394, filed on Oct. 14, 2010, now abandoned.
(Continued)

(51) Int. Cl.
*A01N 47/44* (2006.01)
*A61F 13/00* (2006.01)
(Continued)

(52) U.S. Cl.
CPC ............. *A01N 47/44* (2013.01); *A01N 25/10* (2013.01); *A01N 25/34* (2013.01);
(Continued)

(58) Field of Classification Search
CPC .................................................... A01N 47/44
See application file for complete search history.

(56) References Cited

U.S. PATENT DOCUMENTS 4,343,853 A * 8/1982 Morrison ............... A41D 31/00
                                                        428/905
5,762,797 A    6/1998 Patrick et al.
(Continued)

FOREIGN PATENT DOCUMENTS

EP          1983026 A1    10/2008
JP       2001159029 A      6/2001
(Continued)

OTHER PUBLICATIONS

Merriam-Webster-Miscible. Retreived online 2014.*
(Continued)

*Primary Examiner* — Adam C Milligan
*Assistant Examiner* — Sarah Alawadi

(57) ABSTRACT

Fibrous antimicrobial materials for use in structures and barrier applications, such as face masks and wound dressings, have been developed from antimicrobial polymeric materials. The fibrous antimicrobial materials also are particularly suitable for use in air and water filtration. The antimicrobial polymeric materials are prepared from solid solutions of antimicrobial bisguanide compounds blended with certain thermoplastic polymers. The antimicrobial polymeric materials may be extruded into fibers or used in the particulate form for preparation of the nonwoven antimicrobial materials. The antimicrobial bisguanide compound, such as chlorhexidine, are distributed at the molecular level within at least one thermoplastic polymer, such as a polyolefin in which the antimicrobial bisguanide compound is soluble, to form a miscible blend. Methods for their formation and use also are provided.

11 Claims, 13 Drawing Sheets

Related U.S. Application Data

(60) Provisional application No. 61/325,799, filed on Apr. 19, 2010, provisional application No. 61/251,643, filed on Oct. 14, 2009.

(51) Int. Cl.

| | | |
|---|---|---|
| *A62B 23/02* | (2006.01) | |
| *A01N 25/10* | (2006.01) | |
| *A01N 25/34* | (2006.01) | |
| *A61L 15/24* | (2006.01) | |
| *A61L 15/26* | (2006.01) | |
| *A61L 31/16* | (2006.01) | |
| *C02F 1/00* | (2006.01) | |
| *C08K 5/31* | (2006.01) | |
| *D01F 1/10* | (2006.01) | |
| *D01F 8/04* | (2006.01) | |
| *A61L 15/46* | (2006.01) | |
| *C02F 1/50* | (2006.01) | |

(52) U.S. Cl.
CPC ........ *A61F 13/00063* (2013.01); *A61L 15/24* (2013.01); *A61L 15/26* (2013.01); *A61L 15/46* (2013.01); *A61L 31/16* (2013.01); *A62B 23/025* (2013.01); *C02F 1/004* (2013.01); *C08K 5/31* (2013.01); *D01F 1/103* (2013.01); *D01F 8/04* (2013.01); *A61L 2300/206* (2013.01); *A61L 2300/404* (2013.01); *C02F 1/001* (2013.01); *C02F 1/50* (2013.01)

(56) References Cited

U.S. PATENT DOCUMENTS

| | | |
|---|---|---|
| 6,238,575 B1 | 5/2001 | Patil |
| 6,540,916 B2 | 4/2003 | Patil |
| 6,551,608 B2 | 4/2003 | Yao |
| 6,849,214 B2 | 2/2005 | Patil |
| 6,854,601 B2 | 2/2005 | Patil |
| 7,267,789 B2 * | 9/2007 | Chhabra ................ A61F 13/15 156/167 |
| 7,771,743 B1 | 8/2010 | Luthra et al. |
| 7,850,982 B2 | 12/2010 | Stopeka |
| 2004/0214495 A1 | 10/2004 | Foss et al. |
| 2005/0258093 A1 | 11/2005 | Cueman et al. |
| 2006/0051385 A1 | 3/2006 | Scholz |
| 2007/0006391 A1 * | 1/2007 | Ghosh .................... D01F 1/103 8/115.51 |
| 2007/0044801 A1 * | 3/2007 | Mathis ................... A41D 13/11 128/206.19 |
| 2007/0048344 A1 | 3/2007 | Yahiaoui et al. |
| 2007/0048356 A1 * | 3/2007 | Schorr .................. A01N 47/44 424/443 |
| 2007/0048358 A1 | 3/2007 | Schorr et al. |
| 2007/0270552 A1 | 11/2007 | Zheng |
| 2010/0125105 A1 | 5/2010 | Gooch |
| 2010/0234815 A1 | 9/2010 | Do et al. |

FOREIGN PATENT DOCUMENTS

| | | |
|---|---|---|
| WO | 8602561 A1 | 5/1986 |
| WO | 2007016481 A1 | 2/2007 |
| WO | 2007078203 A1 | 7/2007 |
| WO | 2009064767 A2 | 5/2009 |
| WO | 2010025224 A1 | 3/2010 |

OTHER PUBLICATIONS

PolymerProcessing.com . Polyethylene Melting Temperature 100 Degrees Celsius.*

Laing, Raechel M., Protection Provided by Clothing and Textiles Against Potential Hazards in the Operating Theatre, International J. of Occupational Safety and Ergonomics (JOSE) 2008, vol. 14, No. 1, pp. 107-115.

Behery, Hassan M., Characterization and Testing of Nonwovens with Emphasis on Absorbency, Nonwovens-Theory, Process, Performance & Testing 2007, Chapter 10, pp. 207-228.

International Search Report and Written Opinion PCT/US2010/052608 dated Feb. 3, 2011.

Tallury et al., Poly(ethylene-co-vinyl acetate) Copolymer Matrix for Delivery of Chlorhexidine and Acyclovir Drugs for Use in the Oral Environment: Effect of Drug Combination, Copolymer Composition and Coating on the Drug Release Rate, Dental Materials, vol. 23, 2007, pp. 404-409.

* cited by examiner

FIBROUS ANTIMICROBIAL MATERIALS, STRUCTURES, AND BARRIER APPLICATIONS

CROSS-REFERENCE TO RELATED APPLICATIONS

This application claims benefit of U.S. Nonprovisional application Ser. No. 12/904,394, filed Oct. 14, 2010, and U.S. Provisional Application No. 61/325,799, filed Apr. 19, 2010, and U.S. Provisional Application No. 61/251,643, filed Oct. 14, 2009. These applications are incorporated herein by reference.

BACKGROUND

This disclosure is generally in the field of extruded antimicrobial polymeric materials. In particular, this disclosure relates to use of fibers, filaments, nonwoven materials, and woven materials in antimicrobial structures and uses thereof.

Nonwoven and woven materials are used to make a variety of products for use in various industries. There remains a need, however, for such materials having antimicrobial properties to eliminate microorganisms in various applications, including applications requiring an antimicrobial barrier (e.g., wound dressings, face masks, etc). Existing materials rely on use of bactericides such as iodine, chlorine, alcohol and soap. These materials, however, achieve only a limited antimicrobial protection and often are ineffective at eliminating airborne microorganisms.

One conventional biocompatible antimicrobial agent is chlorhexidine. Chlorhexidine is a 1,6-di(4-chlorophenyl-diguanido) hexane having the chemical formula:

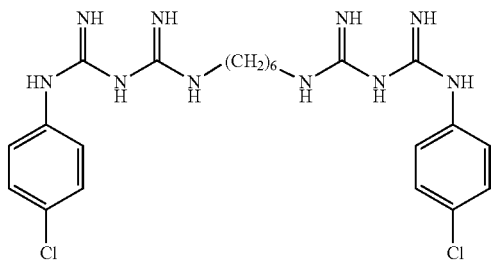

The IUPAC name for chlorhexidine is N,N"Bis(4-chlorophenyl)-3,12-diimino-2,4,11,13-tetrazatetradecanediimideamide. Chlorhexidine has a high level of antibacterial activity and low mammalian toxicity. Historically, chlorhexidine has been used in fluid treatment only in its water-soluble salt forms. When applied to nonwoven materials, these soluble salts are adsorbed into the nonwoven materials and may leach out of the material during use.

The rate of reaction for the soluble chlorhexidine salts or its conventional derivatives is second-order, as the reaction depends on both the concentration of chlorhexidine and the active sites of microorganisms. It would be desirable to provide an antimicrobial material which functions effectively as a zero order reaction.

Accordingly, there remains a need for inexpensive and biocompatible antimicrobial materials for use in nonwoven and woven applications that can effectively inactivate microorganisms in both aqueous liquids and air. It would be desirable for the antimicrobial material to work effectively as an antimicrobial material without being water soluble. It would be further desirable for the material to be readily adaptable for use in various conventional nonwoven and woven applications.

SUMMARY

Novel fibrous antimicrobial materials, devices, and methods are provided herein.

In one aspect, the fibrous antimicrobial material is in the form of a bicomponent antimicrobial fiber comprising a first region of a fibrous antimicrobial material and a second region of the fiber comprising a second polymer. The fibrous antimicrobial material comprises an antimicrobial polymeric material comprising a miscible blend of an antimicrobial bisguanide compound blended with at least one thermoplastic polymer. In one embodiment, the second region is a core of the fiber and the first region is a coating on the core.

In another aspect, a barrier structure is provided comprising at least one layer of a woven or nonwoven fibrous antimicrobial material that is spray impact and fluid penetration resistant. The fibrous antimicrobial material comprises an antimicrobial polymeric material comprising a miscible blend of an antimicrobial bisguanide compound blended with at least one thermoplastic polymer. The miscible blend may comprise from about 1% to about 25% by weight of the antimicrobial bisguanide compound. In one embodiment, the antimicrobial bisguanide compound comprises chlorhexidine and the at least one thermoplastic polymer comprises a polyolefin.

In another aspect, the fibrous antimicrobial material is in an antimicrobial face mask comprising the fibrous antimicrobial material and a means for securing the fibrous material over a person's mouth and/or nose.

In another aspect, the fibrous antimicrobial material is in an antimicrobial wound dressing comprising the fibrous antimicrobial material and a means for securing the fibrous antimicrobial material over a wound of a human or animal.

In still another aspect, the fibrous antimicrobial material is incorporated into a device for antimicrobial treatment of a fluid, the device comprising a filter core with at least one fibrous antimicrobial material wrapped around the filter core.

DETAILED DESCRIPTION

Solid solutions of antimicrobial bisguanide compounds blended with certain thermoplastic polymers have been developed to obtain antimicrobial polymeric materials which can be processed into various forms for use in various applications. The antimicrobial bisguanide compound, such as chlorhexidine, is distributed at the molecular level within at least one thermoplastic polymer, such as a polyolefin in which the antimicrobial bisguanide compound is soluble. In a preferred embodiment, these components are melted and blended together to form a miscible blend, sometimes herein called a polymer alloy. In a preferred embodiment, the blend is cooled to solidify the blend and then the blend is processed into particulate form or directly into fibers. Alternatively, the particles can be processed into fibers. Passage of a fluid having microorganisms through pores in and interstices among the polymer alloy particles or fibers inactivates microorganisms in the fluid. The polymer alloy composition is described in more detail in U.S. Patent Publication No. 2010/00125105, the disclosure of which is incorporated herein by reference in its entirety.

The alloy material provides an improvement over the conventional antimicrobial materials, particularly over applications including soluble bisguanide salts (e.g., chlorhexidine gluconate, etc.), over conventional crystalline bisguanide base forms (e.g., chlorhexidine, etc.), and over bisguanide hydrates, which are described in U.S. Pat. No. 7,427,409. In a preferred embodiment, the alloy material provides an antimicrobial agent in a form which is immobilized with a polymer and which is water-insoluble. The alloy material advantageously may be easily processed into a variety of physical forms such as spun fibers, desirably nonwoven and woven materials prepared therefrom.

Figure 1A:
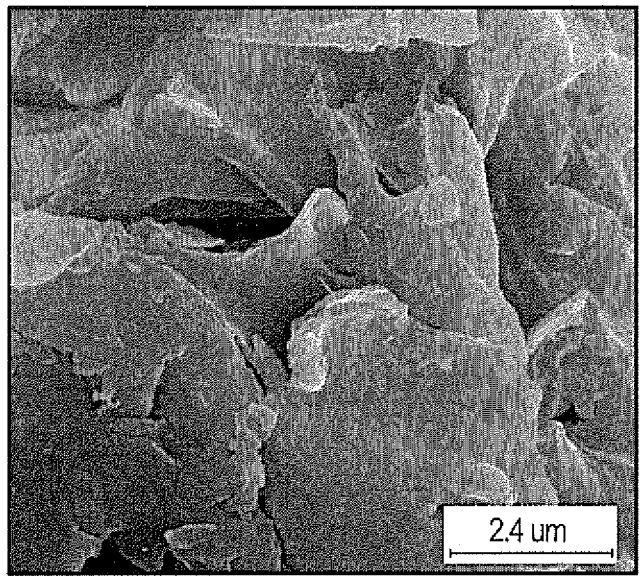
FIGS. 1A and 1B are SEM images of a chlorhexidine-polyethylene composition.
Figure 1B:
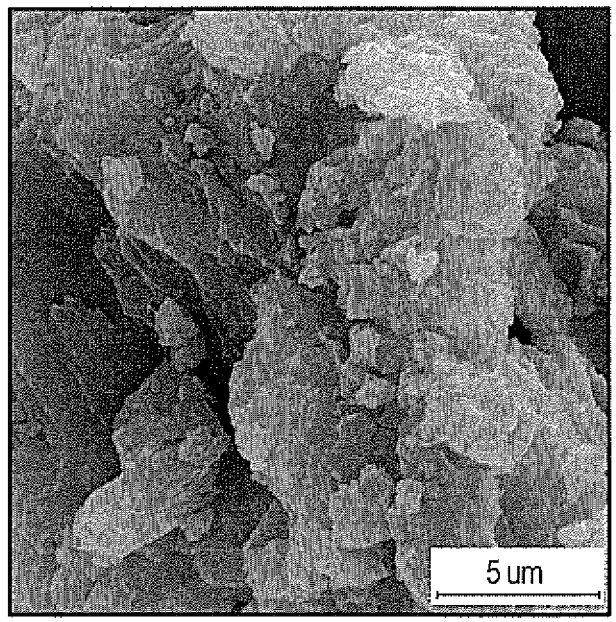

The antimicrobial bisguanide compounds lose their natural morphology upon preparation of the antimicrobial polymeric material. For example, a scanning electron micrograph (FIGS. 1A and 1B) of the cross-section of one embodiment of the antimicrobial polymeric material, a chlorhexidine-polyethylene composition, shows no evidence of the crystalline form of the bisguanide. Not wishing to be bound by any theory, it is believed that the loss of the typical orthorhombic structure of the antimicrobial bisguanide (e.g., chlorhexidine) within the polymer material is due to its chemical and physical compatibility with certain thermoplastic polymers. This compatibility allows for the molecular dispersion of the bisguanide molecules with the polymer molecules, thereby preventing the bisguanide molecules from reforming their natural lattice structures.

The present antimicrobial polymeric materials operate by physical/mechanical contact between the blend material and the microorganisms in the fluid to which it is exposed (whether in gas or liquid form). Microorganisms in the fluid can be inactivated by contact (e.g., transient contact) with the blend material.

As used herein, the term "antimicrobial polymeric material" refers to a blend that comprises at least one antimicrobial bisguanide compound in a solid solution with at least one thermoplastic polymer, wherein the resulting material exhibits antimicrobial activity. The antimicrobial polymeric material desirably is in a nonwoven or a woven material, and may be referred to herein as a "nonwoven antimicrobial material" or a "woven antimicrobial material," respectively. The antimicrobial polymeric material also may be in the form of a drawn fiber material used as a stranded fiber or wound into filaments, and may be referred to herein as a "antimicrobial fiber" or "antimicrobial filament," respectively. The antimicrobial polymeric material also may be in the form of entangled drawn fiber materials. These materials collectively are referred to as "fibrous antimicrobial materials."

The present antimicrobial polymeric materials, nonwoven antimicrobial materials, woven antimicrobial materials and methods of use may be further understood with reference to the following description and accompanying figures.

The Fibrous Antimicrobial Materials and Methods of Use

Fibrous antimicrobial materials are provided that are designed to allow a fluid to pass through a porous structure that includes or consists of the antimicrobial polymeric material. Nonwoven materials, as used herein, include sheet or web-based structures prepared by bonding together fiber or filaments by chemical, mechanical, heat or solvent treatments known to those skilled in the art. Such materials may comprise flat, porous sheets made directly from fibers, molten plastic, or plastic film. Those of ordinary skill in the art will appreciate that unlike woven materials, nonwoven materials are not made by weaving or knitting, and do not require that the fibers be converted into yarn. Woven materials, as used herein, include sheet or web-based structures that are prepared by weaving or knitting fibers or filaments that may be converted into yarn.

The nonwoven and woven antimicrobial materials provided herein may be engineered to have particular properties depending upon the properties required for a desired application. For example, the nonwoven and woven antimicrobial materials may be designed for a specific period of use (single-use or extended use) and/or with other specific features such as adsorbency, absorbency (e.g., by addition of absorbent particles), porosity, resilience, stretch, softness, strength, flame retardance, washability, cushioning, etc. In particular embodiments, the nonwoven and woven materials may be created to mimic the appearance, texture and strength of a woven fabric, and therefore can be used in a variety of different applications, including apparel, health care, and industrial and consumer goods.

Accordingly, the nonwoven and woven antimicrobial material may be in essentially any structure or form depending on the particular application. For example, the nonwoven or woven material may be in the form of a barrier structure configured as a wound dressing in various geometries, face masks, protective clothing, sheet stock, or other structures capable of providing a structural barrier to protect a human or animal from various microorganisms in a contaminated fluid (whether liquid or gas). In still other embodiments the nonwoven and woven antimicrobial material may be in a form suitable for filtration of a contaminated fluid (whether liquid or gas). For example, the structure may be in the form of a water filter or air filter as described in co-pending U.S. Patent Publication No. 2010/00125105, the disclosure of which is incorporated herein by reference in its entirety.

Generally described, the fibrous antimicrobial material comprises an antimicrobial polymeric material. The antimicrobial polymeric material is prepared from a collection of particles which comprise a miscible blend of one or more antimicrobial bisguanide compounds blended with at least one thermoplastic polymer. The antimicrobial bisguanide and thermoplastic polymer may be combined in any amount in which the resulting antimicrobial polymeric material has sufficient antimicrobial activity and retains the structural integrity or porosity needed for a particular use of the antimicrobial polymeric material. In one embodiment, the miscible blend (and resulting antimicrobial polymeric material and the fibrous antimicrobial materials prepared therefrom) is from about 1% to about 25% by weight antimicrobial bisguanide compound. In a preferred embodiment, the miscible blend is from about 5% to about 15% by weight antimicrobial bisguanide compound. Greater or lesser amounts of antimicrobial bisguanide compound may be selected for use in the fibrous antimicrobial material, depending for example on the required mechanical characteristics (e.g., load bearing characteristics, porosity, etc.) that are specified for the particular application in which the fibrous antimicrobial material is to be used.

Figure 2A:
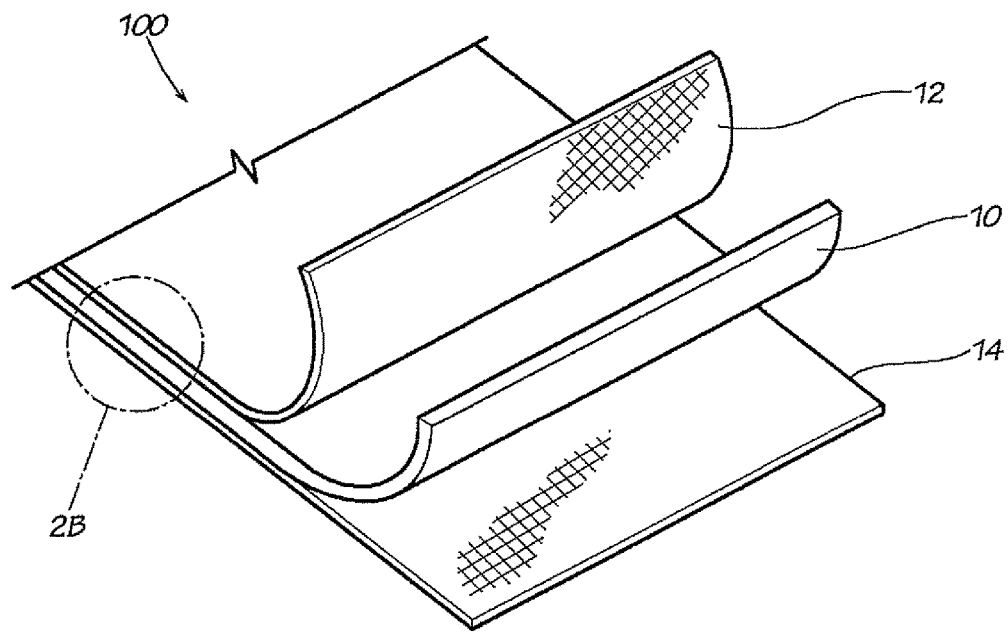
FIGS. 2A and 2B are a schematic illustration and cross-sectional view, respectively, of embodiments of a fibrous antimicrobial material in the form of a multilayer sheet.
Figure 2B:
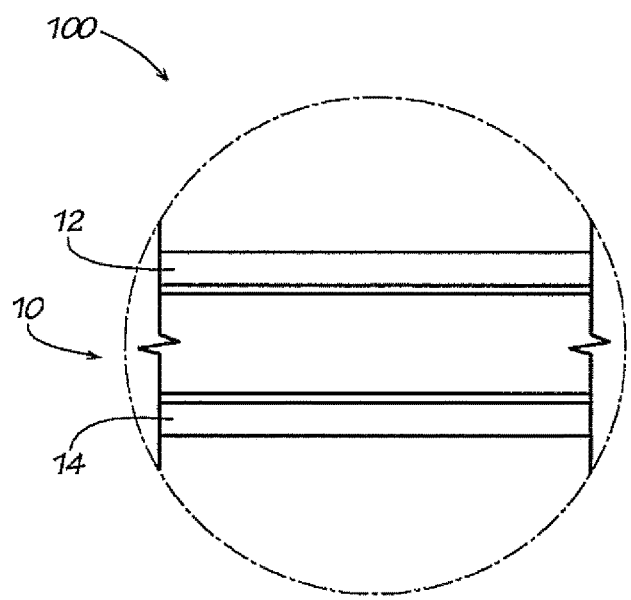

One embodiment of a fibrous antimicrobial material is illustrated in FIGS. 2A and 2B. Generally described, the fibrous antimicrobial materials provided herein are in the form of a sheet or web comprising the antimicrobial polymeric material, such sheets or webs comprising either a single layer material (not illustrated) or a multilayer material (FIGS. 2A and 2B). In one aspect, the fibrous antimicrobial materials may comprise a conventional nonwoven material in the form of a sheet or web in which fine granules or particles of the antimicrobial polymeric material are embedded. In another aspect, the fibrous antimicrobial materials may be formed from fibers of the antimicrobial polymeric material. In such embodiments the fibrous antimicrobial materials optionally may further comprise particles or granules of the antimicrobial polymeric material to enhance the antimicrobial activity of the fibrous antimicrobial material.

Figure 3A:
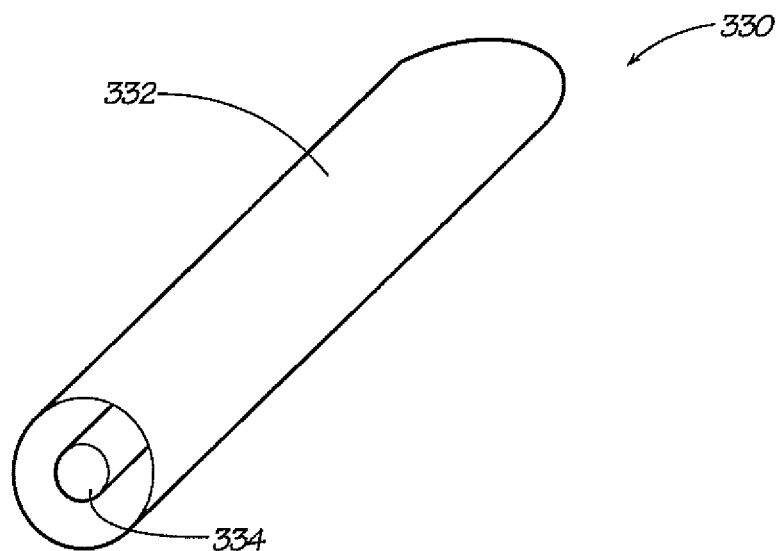
FIGS. 3A and 3B are illustrations of bicomponent fibers comprising an antimicrobial polymeric material according to some embodiments.
Figure 3B:
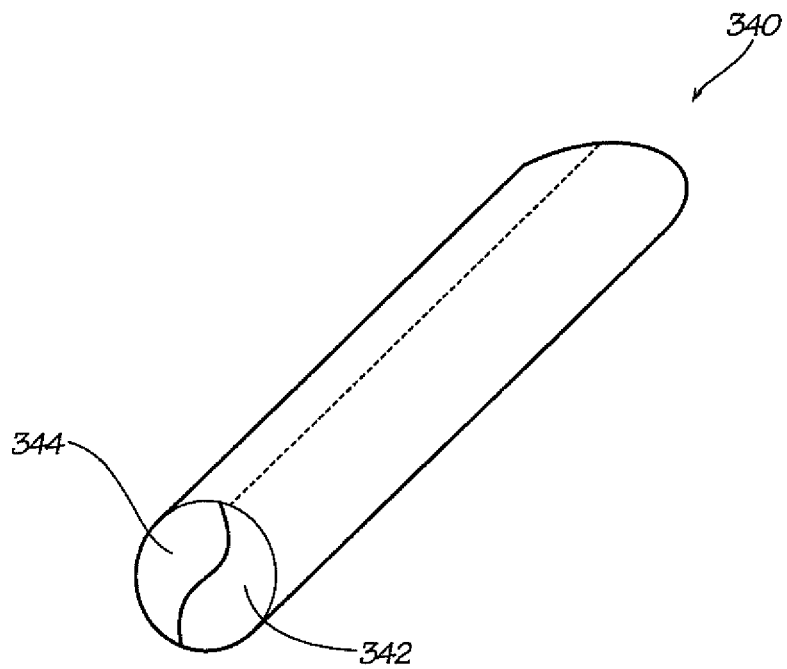

In another aspect, the fibrous antimicrobial materials may be formed from bicomponent fibers comprising the antimicrobial polymeric material. A bicomponent fiber (FIGS. 3A and 3B), as used herein, comprises a fiber having two different polymers in the cross-section (e.g., a concentric/eccentric bicomponent fiber 330 wherein the outer sheath 332 comprises the antimicrobial polymeric material and an inner core 334 comprising a second thermoplastic polymer or a side-by-side bicomponent fiber 340 wherein the antimicrobial polymeric material 342 and second thermoplastic polymer 344 both occupy at least a portion of the fiber surface) in either staple or filament form. In bi-component fibers, the antimicrobial polymeric material desirably comprises from about 5% to about 90% by weight of the fibrous antimicrobial material, from about 5% to about 50% by weight of the fibrous antimicrobial material, or from about 5% to about 30% by weight of the fibrous antimicrobial material. In still another aspect, the fibrous antimicrobial materials may be formed from a combination of fibers of the antimicrobial polymeric material, bicomponent fibers of the antimicrobial polymeric material, fibers of other polymeric materials, and combinations thereof. As used herein, fibrous antimicrobial polymeric materials includes each of the foregoing embodiments.

In a particular embodiment (FIGS. 2A and 2B), the fibrous antimicrobial materials 10 may be included in a multilayer structure 100 having one or more layers of woven or nonwoven materials 12, 14. The one or more layers of woven or nonwoven materials 12 may comprise any woven or nonwoven material suitable for use in the particular application in which the multilayer structure 100 is intended to be used. Those of ordinary skill in the art should appreciate that the one or more other layers of the structure 10 may comprise any suitable woven or nonwoven material, and may include conventional materials used for fluid/air treatment (e.g., activated carbon, wood fiber, etc.) or other antimicrobial compounds than those of the nonwoven antimicrobial materials. For example, in one embodiment the one or more layers of woven or nonwoven materials 12, 14 may be porous, allowing for the flow of moisture through the layer, or may be non-porous, acting as a vapor barrier.

In one embodiment, the antimicrobial bisguanide compound comprises chlorhexidine or a chlorhexidine hydrate. With the chlorhexidine hydrate, the process of making the antimicrobial polymeric material may result in the loss of the water molecule(s) from the chlorhexidine hydrate, to yield the neat form of chlorhexidine in the antimicrobial polymeric material. In a preferred embodiment, the antimicrobial bisguanide compound is in an amorphous form in the blend. In one embodiment, the thermoplastic polymer includes one or more polyolefins. Non-limiting examples of suitable polyolefins include polyethylenes (e.g., low density polyethylene, linear low density polyethylene), polyesters (polyetheylene terephthalate, polybutylene terephthalate, polypropylene terephthalate) and polypropylenes (e.g., low density polypropylene, linear low density polypropylene).

The antimicrobial polymeric materials are believed to have surface properties that are antimicrobial due to the presence of the antimicrobial bisguanide compound which is immobilized with the polymer chain network. Not wishing to be bound by any theory, it is believed that these same surface properties are imparted to fibrous antimicrobial materials comprising the antimicrobial polymeric material. These materials should retain their antimicrobial activity until they are fouled, which is a common mode of failure for any surface active materials known to those of skill in the art. Accordingly, in particular embodiments the antimicrobial polymeric material may be used in combination with other materials and devices known in the art of fluid/air treatment (e.g., activated carbon, wood fibers, etc.).

In another aspect, a method is provided for providing an antimicrobial barrier for inactivating microbiological contaminants in a fluid/air using the nonwoven antimicrobial materials provided herein.

1. the Antimicrobial Bisguanide Compound.

Suitable bisguanide compounds exhibit antimicrobial activity. The term "antimicrobial activity" refers to the property or capability of a material to inactivate microorganisms. Non-limiting examples of microorganisms include bacteria, fungi, and viruses. This "inactivation" renders the microorganism incapable of reproducing and therefore incapable of infecting other organisms and occurs by disruption of the bacteria, fungi or protozoa membrane, or by denaturization of the protein such as that which forms the protective capsid for viruses. While not wishing to be bound by any theory, it is believed that the antimicrobial activity of the bisguanide compound is due to its highly cationic nature. Generally, microorganisms have cell membranes composed of lipids and proteins. When the microorganisms are exposed to the bisguanide compositions, the microorganisms experience a change in surface charge in the cell membrane sufficient to disrupt the cell membrane and render the microorganisms incapable of reproduction In one embodiment, the bisguanide compound exhibits broad spectrum antimicrobial activity. The term "broad spectrum antimicrobial activity" refers to the property or capability of a material to inactivate numerous different, or substantially all, types of microorganisms including bacteria (and its corresponding spores), fungi, protozoa and viruses. An antimicrobial agent that inactivates only a select group of microorganisms (e.g., either only gram positive cells or only gram negative cells) does not have broad spectrum antimicrobial activity.

In a preferred embodiment, the antimicrobial bisguanide compound is water insoluble The term "water insoluble" refers to substantial insolubility in aqueous fluids, particularly aqueous fluids having a pH in the range of about 3 to about 11 at a temperature of about 25° C., such as between about 4 and about 9, and particularly in the range of 6.0 to 8.0. Substantial insolubility may be indicated by measuring less than 0.01% (weight by volume) of the bisguanide compound using conventional detection methods and tools.

In one embodiment, the antimicrobial bisguanide compound is chlorhexidine, which is not a water soluble salt of chlorhexidine.

In another embodiment, the antimicrobial polymeric materials may include at least one of the bisguanide hydrates described in U.S. Pat. No. 7,427,409 or in co-pending U.S. Patent Publication No. 2010/00125105, the disclosures of which are incorporated herein by reference. Tautomers of such bisguanide compounds may also be suitable.

In one embodiment, the bisguanide compound includes a bisguanide hydrate having the chemical formula (Formula I):

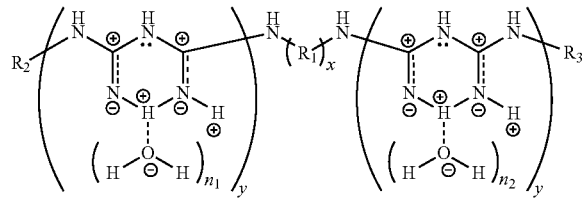

wherein $R_1$ comprises a straight chained, branched, or cyclic alkyl group which may be further substituted with any moieties such as hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximino, hydrazino, carbamyl, phosphonic acid, phosphonato, or any other viable functional group;

wherein $R_2$ and $R_3$, independent of one another, comprise a hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximino, hydrazino, carbamyl, phosphonic acid, phosphonato, or a straight chained, branched, or cyclic alkyl, alkenyl, alkynyl, aryl, heteroaryl, or heterocyclic group, which may be further substituted with any moieties such as hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximino, hydrazino, carbamyl, phosphonic acid, phosphonato, or any other viable functional group;

wherein $n_1$ and $n_2$, independent of each other, are numbers from 0 to 1; and wherein x and y, independent of each other, are numbers from 1 to 3000.

In certain embodiments, y is a number from 1 to 4, and x is a number from 1 to 100, from 1 to 20, from 1 to 10, or from 1 to 8. In one embodiment, the composition has a degree of hydration greater than 0 and less than 2y.

In one embodiment, the compound having the chemical Formula I comprises a bisguanide hydrate in which $n_1$ and $n_2$ are 1 having the chemical formula:

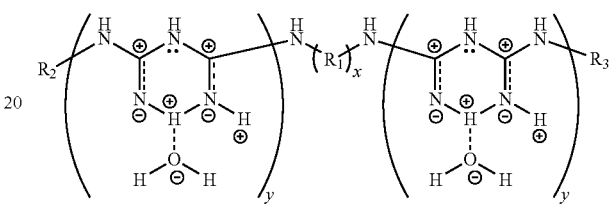

wherein $R_1$ comprises a straight chained, branched, or cyclic alkyl group which may be further substituted with any moieties such as hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximino, hydrazino, carbamyl, phosphonic acid, phosphonato, or any other viable functional group;

wherein $R_2$ and $R_3$, independent of one another, comprise a hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximino, hydrazino, carbamyl, phosphonic acid, phosphonato, or a straight chained, branched, or cyclic alkyl, alkenyl, alkynyl, aryl, heteroaryl, or heterocyclic group, which may be further substituted with any moieties such as hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximino, hydrazino, carbamyl, phosphonic acid, phosphonato, or any other viable functional group; and wherein x and y, independent of each other, are numbers from 1 to 3000. In some embodiments, y is a number from 1 to 4, and x is a number from 1 to 100, from 1 to 20, from 1 to 10, or from 1 to 8. In one embodiment, the composition has a degree of hydration greater than 0 and less than 2y.

In selecting suitable or viable substitutions, the functional group desirably does not eliminate or substantially impair the antimicrobial activity or chemical stability of the compound. For example, $R_1$ generally should not be an unsaturated compound because it would prevent the transfer of electrons via double or triple bonds, disturbing the tautomerism on each side of the bisguanide that is responsible for the partial charge of the guanide groups. $R_1$ may, however, include an isolated double or triple bond non-conjugated with other carbon atoms and with a single bond carbon atom (or more than one carbon atom) adjacent the guanide groups because the double or triple bond would not have electronic communication with the guanide groups and would not interfere with the tautomerism necessary for stabilization of the partial charges on each of the guanide groups. A further example relates to functional groups $R_2$ and $R_3$, which should be electron-withdrawing groups which are capable of assisting in the stabilization of the compound.

In one particular embodiment, the bisguanide hydrate of Formula I comprises chlorhexidine hydrate, having the chemical formula

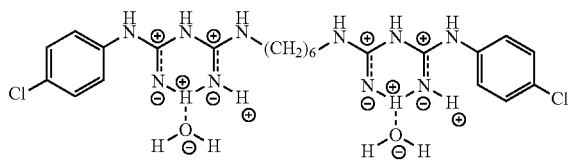

wherein $R_1$ is methylene, $R_2$ and $R_3$ each are a chlorophenyl, $n_1$ is 1, $n_2$ is 1, x is 6, and y is 1. In a particular embodiment, the composition has a degree of hydration that is greater than 0 and less than 2.

In another embodiment of the bisguanide hydrate of Formula I, $R_2$ and $R_3$, independent of one another, are electron-withdrawing groups.

In still other embodiments of the bisguanide hydrate of Formula I, $R_2$ and $R_3$ are independently aryls, are independently substituted aryls, or are independently phenyls. In another embodiment of the bisguanide hydrate of Formula I, $R_2$ and $R_3$ are independently substituted phenyls. The independently substituted phenyls may have ortho, para, or meta substitutions. The independently substituted phenyls may be identical to or different from one another.

In still another embodiment of the bisguanide hydrate of Formula I, $R_2$ and $R_3$ are independently substituted halo phenyls. The independently substituted halo phenyls may have ortho, para, or meta substitutions. The independently substituted halo phenyls may be identical to or different from one another.

In various other examples of the bisguanide hydrate of Formula I, $R_2$ and $R_3$ may independently be substituted halogens, substituted amines, substituted amides, substituted cyanos, or substituted nitros.

In other embodiments, the bisguanide compound includes the "neat" bisguanide composition having the chemical formula (Formula II):

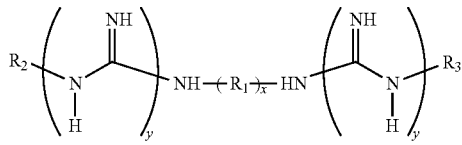

wherein $R_1$ comprises a straight, chained, branched, or cyclic alkyl group which may be further substituted with any moieties such as hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximino, hydrazino, carbamyl, phosphonic acid, phosphonato, or any other viable functional group;

wherein $R_2$ and $R_3$, independent of one another, comprise a hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximino, hydrazino, carbamyl, phosphonic acid, phosphonato, or a straight, chained, branched, or cyclic alkyl, alkenyl, alkynyl, aryl, heteroaryl, or heterocyclic group, which may be further substituted with any moieties such as hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximino, hydrazino, carbamyl, phosphonic acid, phosphonato, or any other viable functional group;

wherein x and y, independent of each other, are numbers from 1 to 3000. In certain embodiments, y is a number from 1 to 4, and x is a number from 1 to 100, from 1 to 20, from 1 to 10, or from 1 to 8.

Where the bisguanide compound has at least four carbon-nitrogen double bonds (e.g., y≥2), hydrogen bonding results in the formation of a heterocyclic structure having the chemical formula of Formula III:

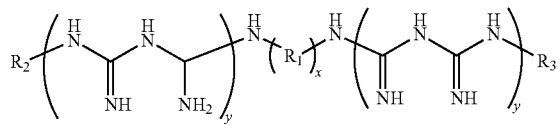

wherein $R_1$ comprises a straight, chained, branched, or cyclic alkyl group which may be further substituted with any moieties such as hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximino, hydrazino, carbamyl, phosphonic acid, phosphonato, or any other viable functional group;

wherein $R_2$ and $R_3$, independent of one another, comprise a hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximino, hydrazino, carbamyl, phosphonic acid, phosphonato, or a straight chained, branched, or cyclic alkyl, alkenyl, alkynyl, aryl, heteroaryl, or heterocyclic group, which may be further substituted with any moieties such as hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximino, hydrazino, carbamyl, phosphonic acid, phosphonato, or any other viable functional group; and wherein x and y, independent of each other, are numbers from 1 to 3000.

In a particular embodiment, the antimicrobial bisguanide compound of Formula III comprises chlorhexidine, a compound having the chemical formula

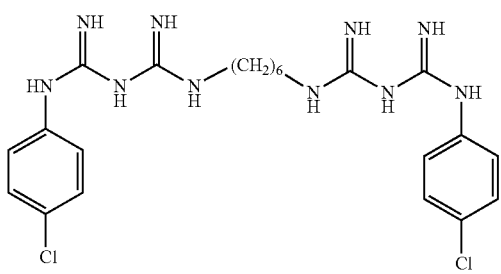

wherein $R_1$ is a methylene, $R_2$ and $R_3$ each are a chlorophenyl, x is 6, and y is 1.

Not wishing to be bound by any theory, it is believed that the antimicrobial bisguanide compounds provided herein form the heterocyclic ring structure below.

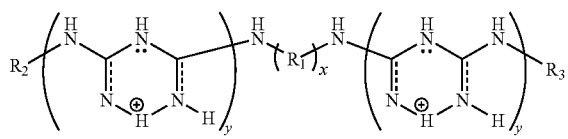

Accordingly, those skilled in the art will appreciate that the antimicrobial bisguanide compounds provided herein include their tautomers.

2. The Thermoplastic Polymer.

The thermoplastic polymer material of the antimicrobial polymeric material generally is selected taking into consideration its ability to form a molecular mixture. That is, the thermoplastic polymer and antimicrobial bisguanide should have sufficient molecular interactions with each other to permit distribution and immobilization of the antimicrobial bisguanide between the polymer chains. The molecular interactions, as used herein, include chemical interactions other than covalent bonds. Examples of such interactions include hydrogen bonding, Van der Waals forces, and other dispersive forces which would be expected between molecularly distributed compositions. In a preferred embodiment, the antimicrobial bisguanide and the thermoplastic polymer are substantially miscible with one another. In this way, the antimicrobial bisguanide can be distributed at the molecular level throughout the polymer. That is, the antimicrobial polymeric material may include a molecular mixture of these two components.

"Substantially soluble" or "substantially miscible" as used herein refers to the ability of the antimicrobial bisguanide to dissolve in a fluidized form of the thermoplastic polymer, such as a polymer melt, or in a solution of the polymer and an organic solvent. Thus, a "miscible blend" as used herein refers to a molecular mixture of two or more components.

Depending upon the process used to make the antimicrobial polymeric material, the melting temperature of the polymer may be an important factor in the selection of a suitable polymer material. In one embodiment, the melting temperature of the thermoplastic polymer must be such that the antimicrobial bisguanide compound is capable of mixing with the thermoplastic polymer when it is in its liquid state without being so high that the antimicrobial bisguanide degrades to a significant extent before the antimicrobial polymeric material can be cooled. In one embodiment, the thermoplastic polymer has a melting temperature below about 165° C., more particularly below about 135° C., and still more particularly below about 120° C. In other embodiments, the thermoplastic polymer may have a higher melting temperature if the polymer can be transformed into a liquid state without heating, e.g., by forming a solution with a suitable solvent, or if the heated polymer melt can be cooled rapidly enough to avoid substantial degradation of the components following mixing.

Representative examples of suitable thermoplastic polymer materials include polyolefins, polyethylenes such as ethylene adipate, ethylene oxide, low density polyethylene, linear low density polyethylene, and high density polyethylene, polyesters such as polyetheylene terephthalate, polybutylene terephthalate, polypropylene terephthalate, and polycaprolactone, polypropylenes such as low density polypropylene and linear low density polypropylene, and vinyl polymers such as ethyl vinyl ether, propyl vinyl ether, vinyl acetal, vinyl butyral, and butyl vinyl ether. In particular embodiments, thermoplastic polymers having melting temperatures above 120° C. (e.g., polyurethanes) may be combined with additives (e.g., plasticizers) to reduce the melting temperature of the polymer to a sufficiently low temperature to avoid substantial degradation of the antimicrobial bisguanide compound.

One of skill in the art can readily select other suitable polymers for use in the present antimicrobial polymeric materials, for example, by taking into consideration the component selection characteristics and antimicrobial polymeric material features described above. Those skilled in the art will appreciate that the solubility of two or more components may be determined using empirical models which evaluate the intermolecular forces between the solvent and the solute and the entropy change accompanying the solvation. For example, the Hansen Solubility Parameters of each component may be calculated from three-dimensional solubility coefficients which account for the dispersion bonds, polar bonds, and hydrogen bonds between molecules. The three parameters can be treated as coordinates for a point in three dimensions such that the nearer two molecules are in the three dimensional space, the more likely they are to dissolve in each other. The Hildebrand Solubility Parameter ($\delta$) also provides a means of evaluating the probable solubility of compositions, where materials with similar values of $\delta$ provide a good indication of solubility.

The antimicrobial bisguanide and thermoplastic polymer may be combined in any amounts in which the resulting polymer blend has sufficient antimicrobial activity when used in a fibrous antimicrobial material while not substantially impairing the structural integrity of resulting polymer blend when embodied in a fibrous antimicrobial material. Thus, the antimicrobial bisguanide should be present in an amount sufficient to facilitate contact between any microorganisms which may come into contact with the fibrous antimicrobial material. Those skilled in the art will appreciate, however, that the amount of antimicrobial bisguanide compound can be selected for use in the fibrous antimicrobial material, depending for example on the required mechanical characteristics (e.g., load bearing characteristics, porosity, etc.) that are specified for the particular application in which the fibrous antimicrobial material is to be used.

3. Additional Components in the Blend.

The antimicrobial polymeric material optionally may further include one or more additional components. In one embodiment, the additional component is a plasticizer.

These other components may be miscible or immiscible in the polymer-antimicrobial bisguanide blend.

The additional component may be, for example, in particulate or fiber form. These other components may, for example, be useful in fluid purification, such as carbon, zeolites, etc. They may be homogeneously or heterogeneously distributed in the antimicrobial polymeric material. In one embodiment, the additional component is present in the antimicrobial polymeric material in an amount from about 0.1 wt % to about 20 wt %. In one embodiment, the additional component is a polymer that is coextruded with the polymer alloy. This additional, or second, polymer may be the same as or different from the polymer of the antimicrobial polymeric material. In one case, the second polymer is the core and the antimicrobial polymeric material is the outer layer surrounding the core of a co-extruded fiber. The second polymer preferably is a thermoplastic polymer. Those skilled in the art, however, will appreciate that the addition of one or more additional components should not substantially reduce the surface area of the antimicrobial bisguanide compound in the antimicrobial polymeric material or otherwise impair the antimicrobial activity of the antimicrobial polymeric material.

Methods for Making the Fibrous Antimicrobial Materials

The fibrous antimicrobial materials are prepared from suitable antimicrobial polymeric material using methods known to those skilled in the art.

1. Method for Preparing Antimicrobial Polymeric Material

The antimicrobial bisguanide and thermoplastic polymer may be combined by any suitable means known to those of ordinary skill in the art. Such methods should allow for preparation of a substantially miscible blend in which the antimicrobial bisguanide is substantially undegraded. Thus, the resulting antimicrobial polymeric material is substantially free of destabilized antimicrobial bisguanide or its degradants.

In one embodiment, a method for preparing the antimicrobial polymeric materials comprises melting an antimicrobial bisguanide compound and a thermoplastic polymer with which the antimicrobial bisguanide compound is miscible; mixing the melted antimicrobial bisguanide compound and the melted thermoplastic polymer to form a miscible blend of the antimicrobial bisguanide compound dispersed in the thermoplastic polymer; and cooling the miscible blend to solidify the blend.

Figure 4A:
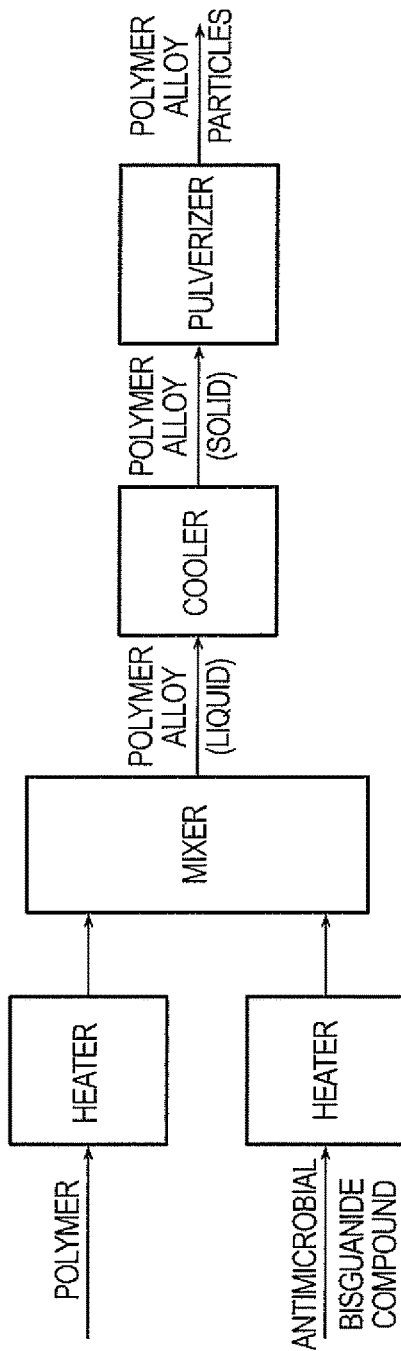
FIGS. 4A and 4B are illustrations of a method for preparing an antimicrobial polymeric material according to some embodiments.
Figure 4B:
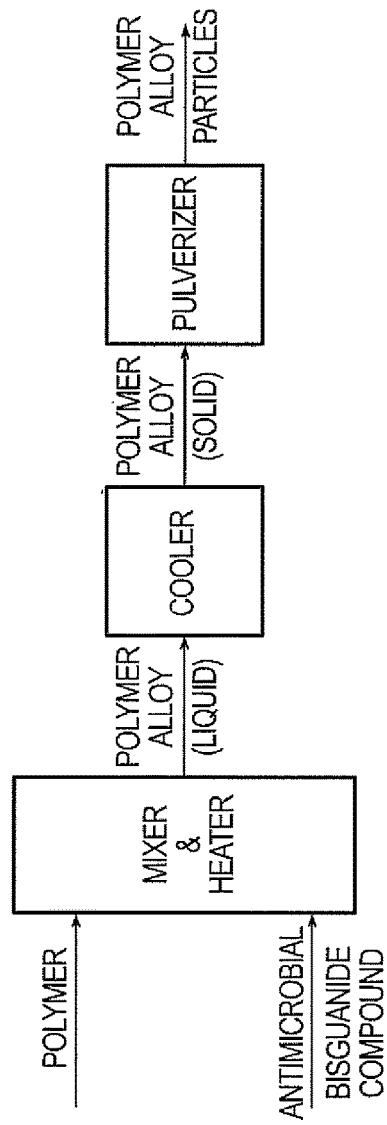

The thermoplastic polymer and antimicrobial bisguanide compound may be melted using any suitable means known to those skilled in the art as long as the antimicrobial bisguanide compound and thermoplastic polymer remain substantially undegraded. That is, the processing temperature must be sufficiently high to melt the thermoplastic polymer without being so high that the antimicrobial bisguanide compound degrades to a significant extent before the antimicrobial polymeric material can be cooled. In one embodiment, the thermoplastic polymer may be melted by heating the thermoplastic polymer above its melting temperature, and the antimicrobial bisguanide compound may be mixed with the melted thermoplastic polymer to form a miscible blend of the antimicrobial bisguanide compound dispersed in the thermoplastic polymer. For example, the thermoplastic polymer and antimicrobial bisguanide compound may be blended before or after melting the thermoplastic polymer and antimicrobial bisguanide compound, as illustrated in FIGS. 4A and 4B.

In another embodiment, the thermoplastic polymer may be dissolved in a suitable solvent and blended with the antimicrobial bisguanide compound. Because of the substantial insolubility of the antimicrobial bisguanide compound, however, such methods may still require heating of the antimicrobial bisguanide compound in order to obtain a miscible blend of the antimicrobial bisguanide compound dispersed in the thermoplastic polymer. Methods for solvent casting of thermoplastic polymers are well known to those skilled in the art.

Figure 5:
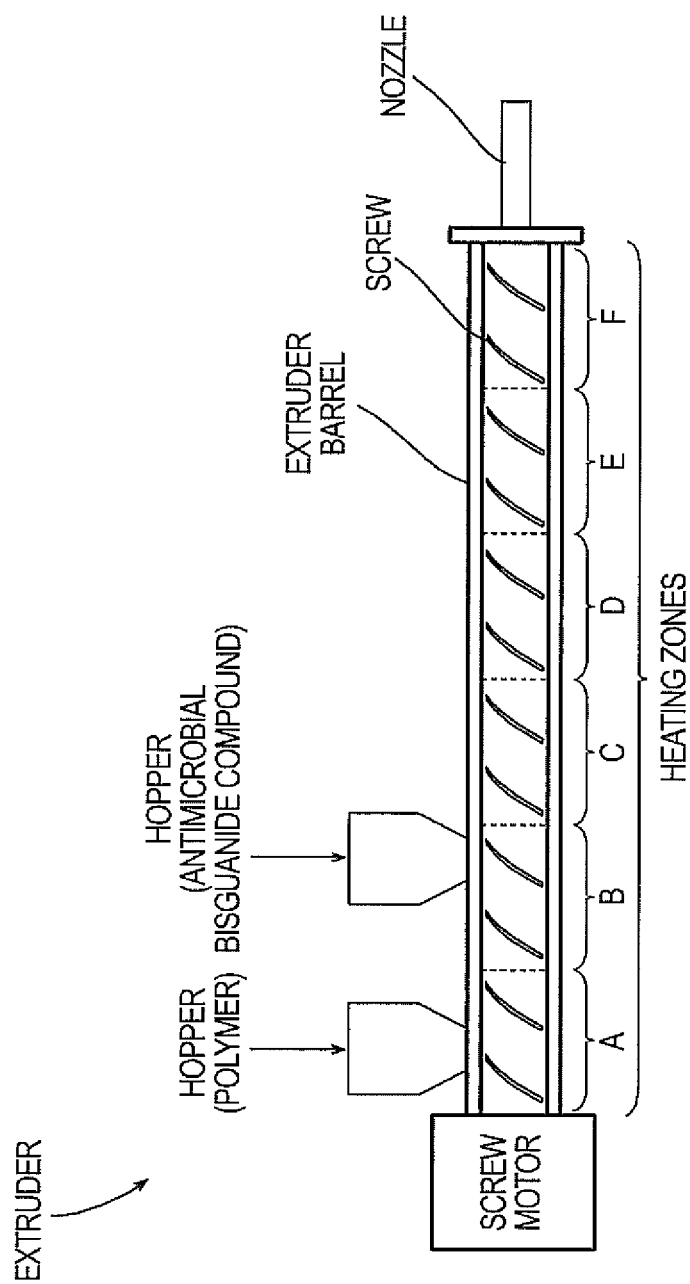
FIG. 5 is an illustration of an extrusion process for preparing an antimicrobial polymeric material according to an embodiment.

In an exemplary embodiment, the method for preparing an antimicrobial polymeric material comprises the extrusion process illustrated in FIG. 5. The extrusion process generally comprises feeding the thermoplastic polymer to the extruder and heating the thermoplastic polymer above its melting temperature to obtain a thermoplastic polymer melt, adding an insoluble antimicrobial material to the thermoplastic polymer melt and vigorously mixing to molecularly disperse the antimicrobial material throughout the thermoplastic polymer, and cooling the temperature of the heated blend to obtain a solid antimicrobial polymeric material. The mixing of the mixture and speed at which the mixture is passed through the extruder may be controlled by modifying the rate of rotation of the rotating screw in the extruder.

The heating profile of the extruder may be controlled using multiple independent controlled heater zones to gradually increase the temperature of the melt and minimize the length of time the mixture is exposed to higher temperatures, thereby minimizing the potential for degradation of the antimicrobial bisguanide compound. Generally, extruders comprise three or more independently controlled heater zones.

The porosity and structure of the antimicrobial polymeric material may be modified during the extrusion process. By increasing the porosity of the antimicrobial polymeric material, the surface area of the antimicrobial bisguanide compound that is exposed also may be increased, thereby enhancing the antimicrobial activity of the antimicrobial polymeric material. For example, use of a blowing agent (e.g., physical or chemical blowing agents, non-limiting examples of which include inert gases such as air and nitrogen) may promote the formation of small voids within the antimicrobial polymeric material. Such voids, however, should not substantially impair the physical integrity of the antimicrobial polymeric material nor the overall surface charge of the antimicrobial polymeric material.

In a particular embodiment, the resulting antimicrobial polymeric material is further processed into particles prior to preparing the fibrous antimicrobial material using methods well known to those of ordinary skill in the art. For example, the polymer blend may be pulverized to obtain particle sizes that are suitable for the desired use, using various size reduction equipment known in the art including, but not limited to, mills, grinders, and the like. In one embodiment, the cooled antimicrobial polymeric material is pulverized to a desired particle size by means of a blender. In another embodiment, the particles are pulverized to a desired particle size using cryogenic methods.

2. Method for Preparing Fibrous Antimicrobial Material

The antimicrobial polymeric material may be processed into fibers and a nonwoven or woven structure (e.g., web, mat, and the like) using methods well known to those of skill in the art. Such methods are described, for example, in U.S. Pat. Nos. 6,548,431; 5,853,883; 5,853,641; 5,633,082; 5,632,944; 4,181,640; and 3,751,332; and U.S. Patent Publication No. 2004/0097158, the disclosures of which are incorporated herein by reference. The fibers may have a linear density from 0.1 to 30 denier.

Figure 6A:
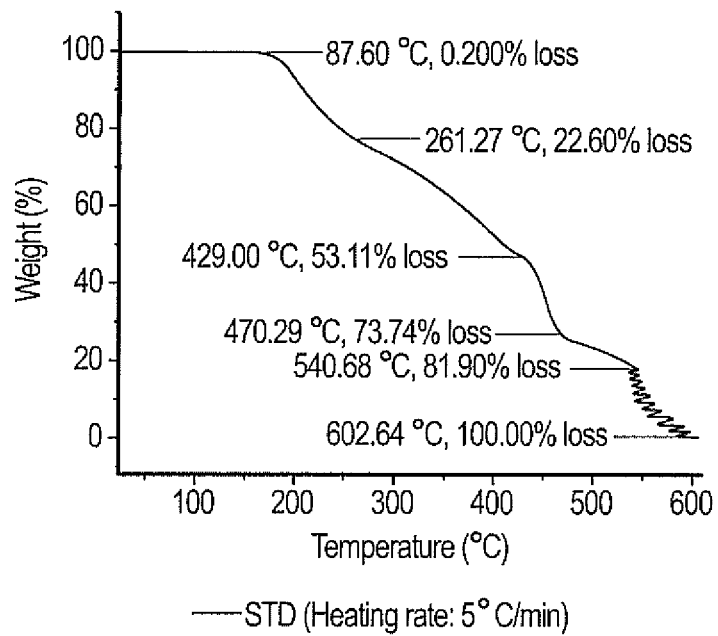
FIGS. 6A and 6B are TGA thermograms of chlorhexidine and chlorhexidine hydrate.
Figure 6B:
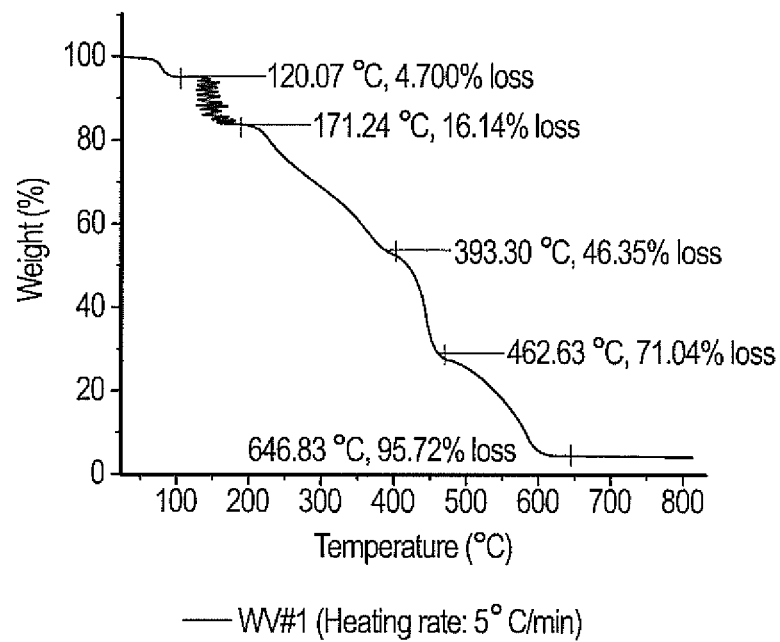
Figure 7A:
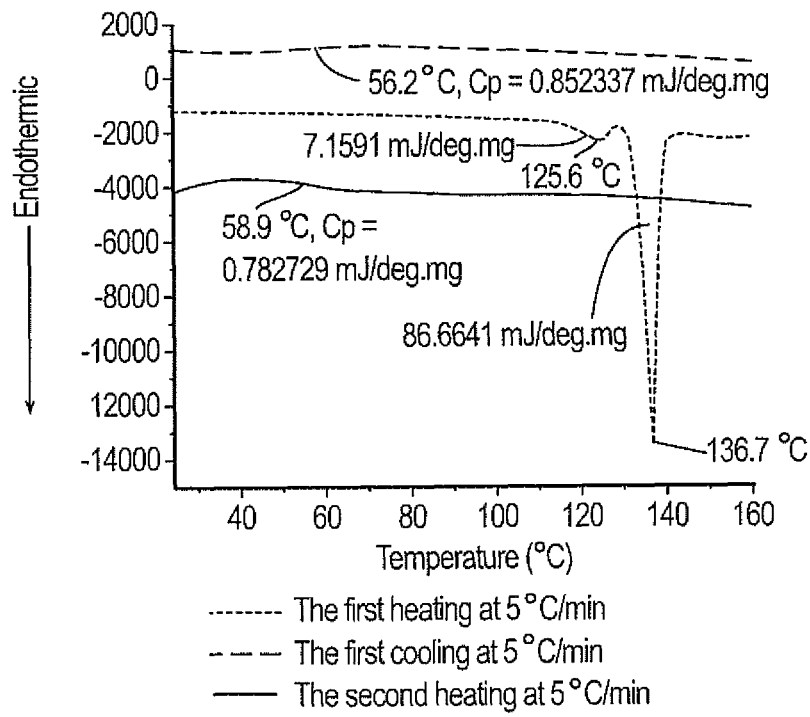
FIGS. 7A and 7B are DSC thermograms of chlorhexidine and chlorhexidine hydrate.
Figure 7B:
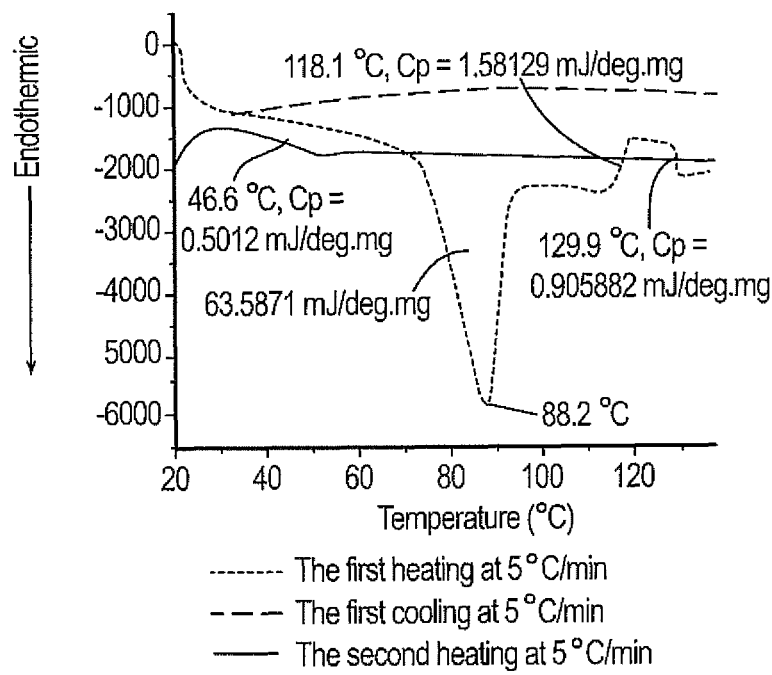

In an embodiment, the processing temperature of any process is sufficiently below the degradation temperature of the antimicrobial bisguanide compound such that there is substantially no degradation of the antimicrobial bisguanide compound. The degradation temperature of the antimicrobial bisguanide compounds may be evaluated by considering the TGA and DSC thermograms of the antimicrobial bisguanide compound. Illustrative TGA thermograms (FIGS. 6A and 6B) and DSC thermograms (FIGS. 7A and 7B) of chlorhexidine and chlorhexidine hydrate, respectively, are provided.

In embodiments in which the antimicrobial bisguanide compound comprises chlorhexidine or a chlorhexidine-based compounds, it is desirable to utilize a high purity chlorhexidine so as to minimize the amount of para-chloroanaline that may be present during production of the fibers. Those skilled in the art will further appreciate, however, that numerous commonly used methods (e.g., venting and use of masks or other respiratory devices) may be used to guard against exposure to any para-chloroanaline that is present in the antimicrobial bisguanide compound or that may be formed as a bi-product during the production of the fibers.

Applications/Uses for the Fibrous Antimicrobial Materials

The fibrous antimicrobial materials described herein have numerous applications. Advantageously, the fibrous antimicrobial materials are of an insoluble and nonconsumable catalytic nature, and may be capable of inactivating a broad spectrum of microorganisms. Generally, the fibrous antimicrobial materials can be used in applications where it is desirable to reduce and/or eliminate microorganisms in a fluid. Nonlimiting examples of such fluids include aqueous solutions, water, air, and other gases. In embodiments, the fibrous antimicrobial materials exhibit at least a 3 $\log_{10}$ reduction of microorganisms, at least a 4 $\log_{10}$ reduction of microorganisms, at least a 5 $\log_{10}$ reduction of microorganisms, or at least a 6 $\log_{10}$ reduction of microorganisms, within a period of less than or equal to about 6 hours, a period of less than or equal to about 60 minutes, a period of less than or equal to about 30 minutes, a period of less than or equal to about 10 minutes, or a period of less than or equal to about 5 minutes after contact with the fibrous antimicrobial materials.

Figure 8:
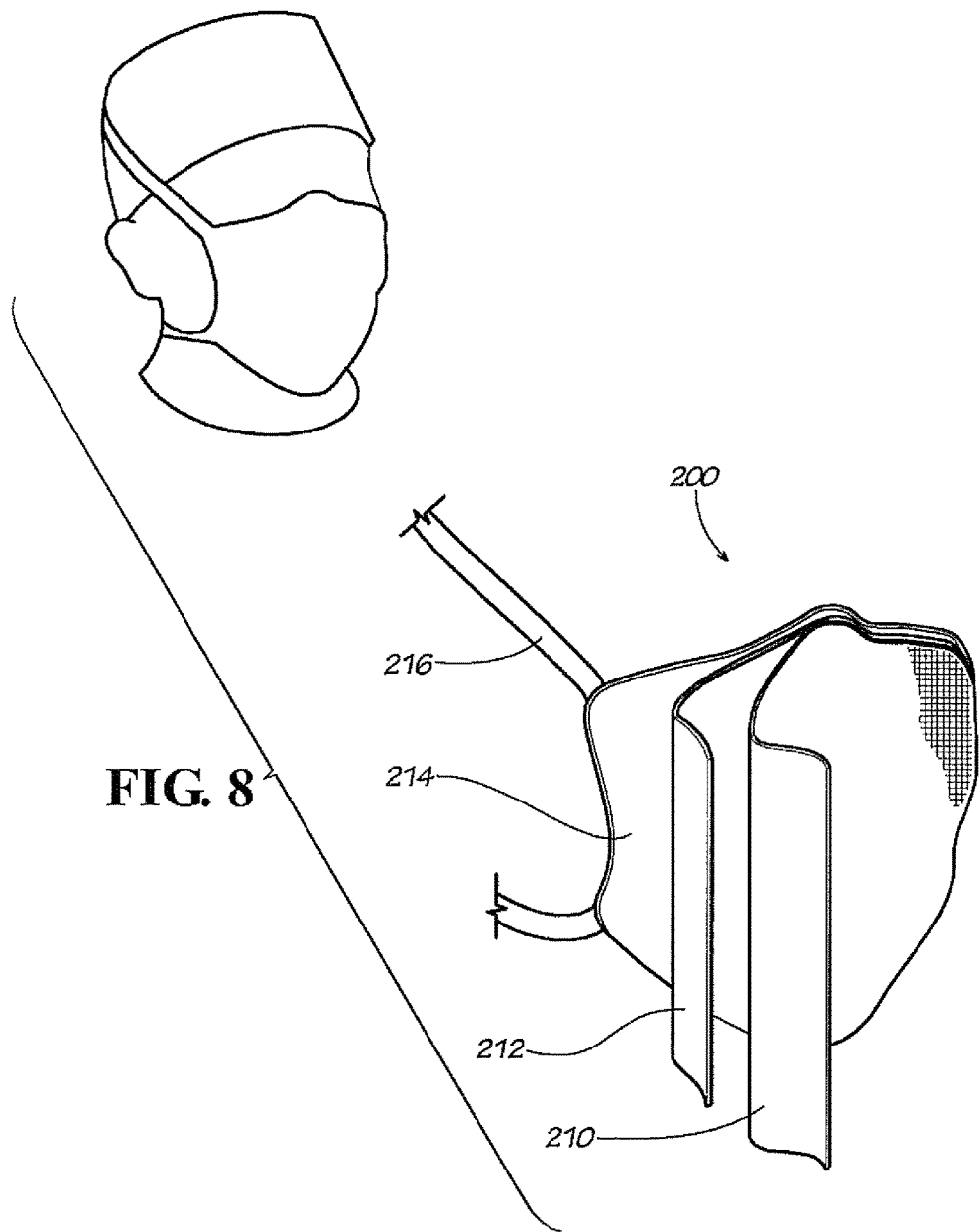
FIG. 8 is a schematic illustration of an embodiment of a protective mask comprising a fibrous antimicrobial material according to an embodiment.

In a particular embodiment, the fibrous antimicrobial materials are incorporated into protective masks, as illustrated in FIG. 8. The protective mask 200 comprises a nonwoven porous top sheet 210, the nonwoven antimicrobial material 212, a nonwoven porous back sheet 214, and tie strings 216 for fastening the mask over the nose and/or mouth of the user. Those of skill in the art will appreciate that numerous other means are known by which the protective mask may be affixed to the wearer, non-limiting examples of which include straps, loops, adhesives, and other flexible members. Those of ordinary skill in the art also should appreciate that the protective shape may be in any suitable shape for covering the wearer's nose and/or mouth. Desirably, the protective mask is a barrier structure and is effective at providing a bacterial filtration efficiency as measured by ASTM F2100 of at least 75%, at least 85%, at least 90%, or at least 95%. Other aspects of protective masks are generally known to those skilled in the art and may be incorporated into embodiments of the protective masks provided herein, non-limiting examples of which are disclosed in U.S. Pat. Nos. 6,062,220 and 4,941,470, the disclosures of which are incorporated herein by reference.

As used herein, "barrier structure" means that the material is spray impact and fluid penetration resistant as characterized, for example, using standardized test methods and performance levels well known to those skilled in the art. Non-limiting examples of such test methods include AATCC 42 (Water Resistance: Impact penetration test) and AATCC 127 (Water Resistance: Hydrostatic pressure test).

In particular embodiments, the barrier structure is characterized as having a fluid barrier characteristic as measured by hydrostatic head testing of equal to or greater than about 20 millibars; equal to or greater than about 50 millibars; or equal to or greater than about 100 millibars.

In still other embodiments, the fibrous antimicrobial materials are incorporated into other barrier structures, non-limiting examples of which include garments (e.g., surgical gown, robe, masks, head covers, shoe covers, gloves), surgical drapes, surgical fenestration or cover, sheets, bedclothes, padding, gauze dressings, or disposable cloth for use in personal care applications (e.g., sponges, baby wipes, personal wipes, facial wipes, etc.). These materials may be prepared from the nonwoven antimicrobial materials or from woven antimicrobial materials prepared from filaments of the antimicrobial material resembling yarns. These filaments may be woven into fabrics using processes and procedures generally known to those skilled in the art.

Figure 9:
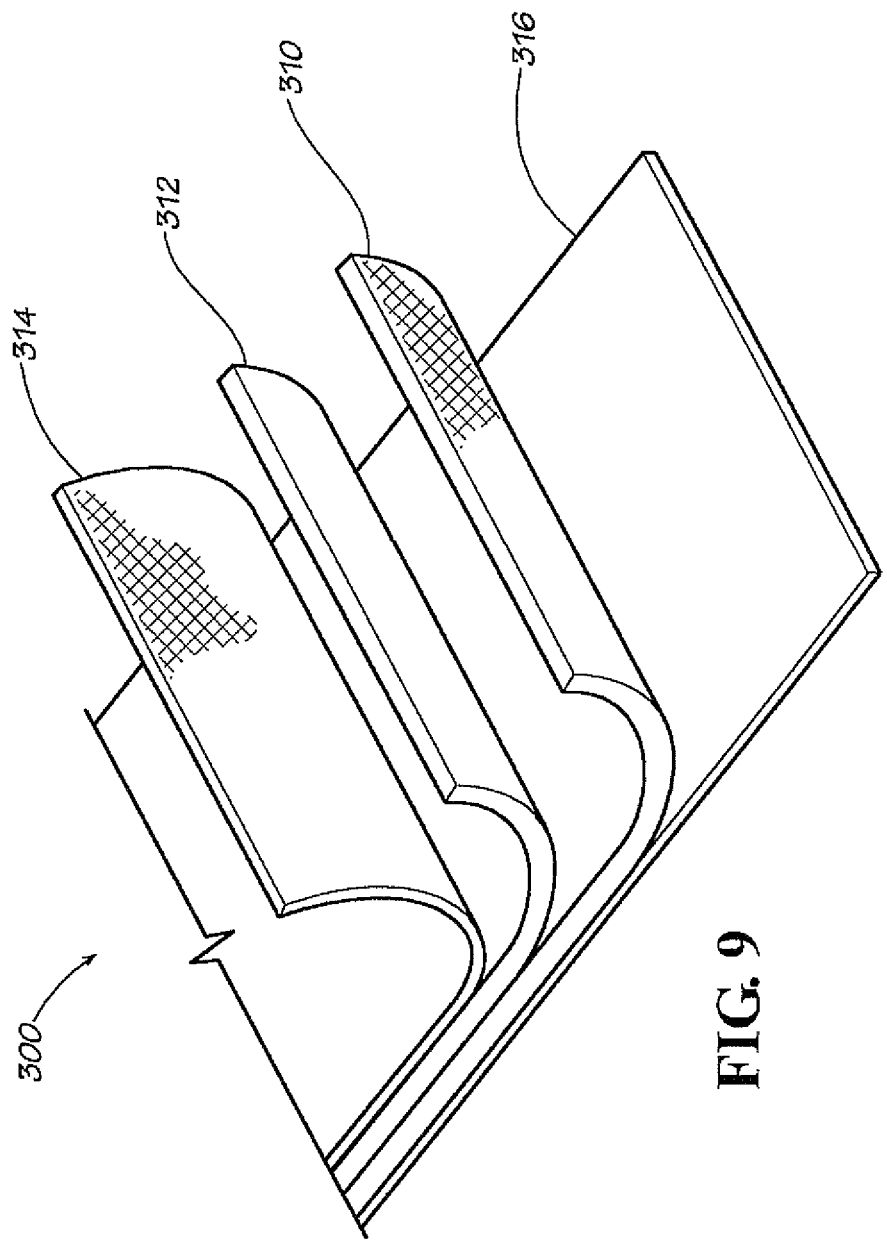
FIG. 9 is a schematic illustration of a wound dressing comprising a fibrous antimicrobial material according to an embodiment.

In a particular embodiment, the fibrous antimicrobial materials embodied in the present description are incorporated into wound dressings, as illustrated in FIG. 9. The wound dressing 300 comprises a nonwoven porous or nonporous top sheet 310, an absorbent core 312 comprising the antimicrobial nonwoven material, and a nonwoven porous back sheet 314. The absorbent core 312 may comprise a nonwoven material in which particles or granules of the antimicrobial polymeric material are embedded or may comprise a nonwoven web or sheet of the antimicrobial polymeric material. The absorbent core 312 may further comprise one or more other materials, such as a superabsorbent material. Superabsorbent materials are known to those skilled in the art, and include natural and synthetic materials capable of absorbing and retaining extremely large amounts of a liquid relative to their mass. In particular embodiments, the wound dressing 300 may further comprise a means for affixing 316 the dressing to the wearer, for example by an adhesive. Other aspects of wound dressings are generally known in the art and may be incorporated into embodiments of the wound dressings provided herein, non-limiting examples of which are disclosed in U.S. Pat. Nos. 7,576,256; 7,270,721; and 6,160,196 and U.S. Patent Publication No. 2004/0082925, the disclosures of which are incorporated herein by reference.

In one embodiment, the antimicrobial polymeric material is in the form of a sterile barrier structure. The material may be sterilized using methods known in the art, including gamma or e-beam irradiation or treatment with ethylene oxide or other chemical sterilants known in the art. The barrier structure may be sterilized prior to or after packaging for transport and storage, e.g., in flexible, sealed foil or film packaging.

In still other embodiments, the antimicrobial polymeric materials are incorporated into medical devices (e.g., stents, sutures, meshes, shunts, drains, catheters, tubes, nonwovens, or other medical devices that would benefit from having a broad spectrum antimicrobial activity). The antimicrobial polymeric materials and/or fibrous antimicrobial materials may be incorporated into such medical devices using processes and procedures generally known to those skilled in the art.

In still other embodiments, the antimicrobial polymeric materials are incorporated into porous and nonporous films and coatings, such as a non-porous barrier layer, using processes and procedures generally known to those skilled in the art.

Figure 10:
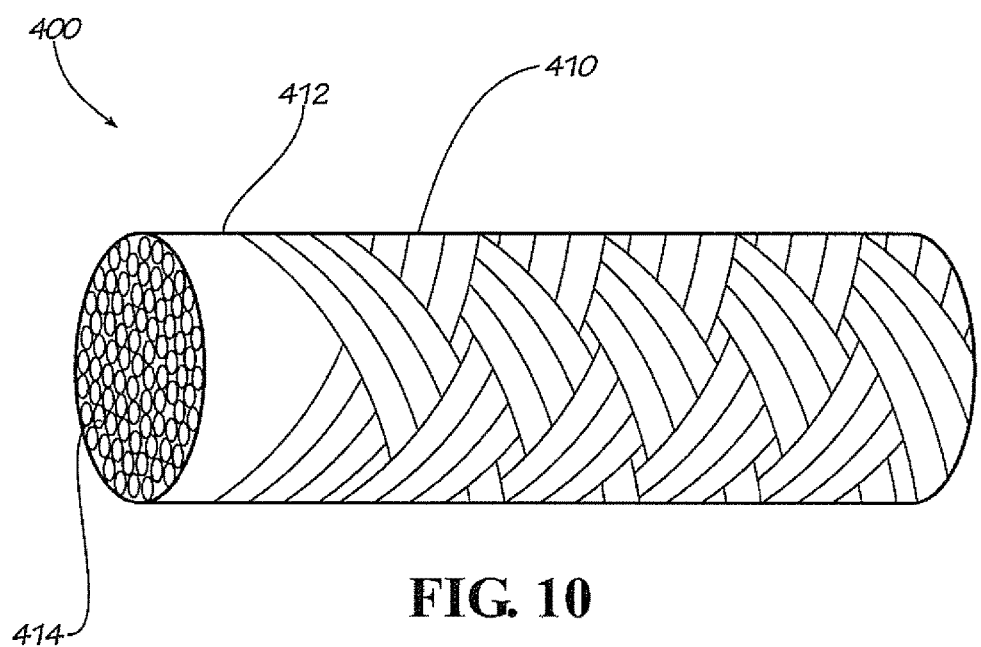
FIG. 10 is a schematic illustration of a device for filtration comprising the fibrous antimicrobial material according to an embodiment.

In still other embodiments (FIG. 10), the fibrous antimicrobial materials are incorporated into filament wrapped filters 400 that may have a variety of shapes and sizes depending on the desired application. The filaments are prepared from spun fibers that have been spun to a desired tightness and porosity. These filaments 410 are then wrapped on a suitable core material 412, using methods known to those skilled in the art. The method of wrapping and tightness of the filament may be modified as needed to provide desirable filter characteristics and antimicrobial activity.

In still other embodiments, the fibrous antimicrobial materials are incorporated into materials and devices comprising other materials suitable for filtration and/or purification of contaminated fluids (e.g., carbon, hydroxylapatite, etc.). For example, in one embodiment the other materials suitable for filtration and/or purification of contaminated fluids may be in the form of particles packed within the core 412 of the filament wrapped filters 400, with the other materials comprising an activated carbon/hydroxyalapatite mixture as described in U.S. Pat. No. 6,187,192, the disclosure of which is incorporated herein by reference. The activated carbon may be derived from any suitable source, non-limiting examples of which include bituminous based coal, wood-based carbons, bone-char carbon, and coconut shell carbon. Coconut shell carbon is particularly desirable for use in filtration devices because it has a substantially higher micropore volume than other carbons, providing a greater surface area and higher porosity. For example, activated coconut shell carbon provides about 50% more micropores than bituminous coal-based activated carbon. Coconut shell carbon also has other beneficial attributes making it particularly suited for use in filtration devices.

The devices, compositions, and methods described above will be further understood with reference to the following non-limiting examples.

Example 1: Preparation of a Polyethylene Blend

A 150 mL beaker was equipped with a mechanical stirrer and placed in an oil bath equipped with a thermostat. A specified amount of a low density polyethylene (LDPE) was placed into the beaker and heated to 150° C. with stirring. A specified amount of chlorhexidine hydrate was added to the melted polyethylene, heated for an additional 10 minutes with stirring, and then cooled to room temperature. The resulting mixture cooled to a hard, white solid that was collected, pulverized in a laboratory blender, and placed in a glass vial covered with argon gas.

The amounts of the polyethylene and chlorhexidine hydrate used in each sample are set forth below.

TABLE 1

Composition of blend samples

| Sample | Polyethylene mass (% by weight) | Chlorhexidine Hydrate mass (% by weight) |
|---|---|---|
| 1 | 28.5 (95) | 1.5 (5) |
| 2 | 27.0 (90) | 3.0 (10) |
| 3 | 25.5 (85) | 4.5 (15) |
| 4 | 24 (80) | 6 (20) |

Example 2: Preparation of a Polystyrene Blend

A 150 mL beaker was equipped with a mechanical stirrer and placed in an oil bath equipped with a thermostat. A specified amount of polystyrene (PS) was placed into the beaker and heated to 210° C. with stirring. Upon heating, the polystyrene was white with a slight discoloration due to thermal decomposition. A specified amount of chlorhexidine hydrate was added to the melted polystyrene, heated for an additional 10 minutes with stirring, and then cooled to room temperature. The resulting mixture cooled to a hard, white solid with discoloration that was collected, pulverized in a laboratory blender, and placed in a glass vial covered with argon gas.

The amounts of the polystyrene and chlorhexidine hydrate used in each sample are set forth below.

TABLE 2

Composition of blend samples

| Sample | Polystyrene mass (% by weight) | Chlorhexidine Hydrate mass (% by weight) |
|---|---|---|
| 1 | 28.5 (95) | 1.5 (5) |
| 2 | 27.0 (90) | 3.0 (10) |
| 3 | 25.5 (85) | 4.5 (15) |
| 4 | 24 (80) | 6 (20) |

Although soluble and effective for forming a polymer matrix with the chlorhexidine hydrate, the processing temperature for polystyrene (PS) was too high and caused a yellowing color due to the partial thermal decomposition of the bisguanide. Although processing of the polyethylene and chlorhexidine hydrate blend on a lab scale did not immediately cause discoloration, extrusion on a larger scale (75 lbs.) caused some slight yellowing effect in the appearance, indicating there was at least some degradation of the antimicrobial bisguanide compound and that the processing temperatures needed to be further optimized.

Example 3: Preparation of Polyurethane Blends

Polyurethanes also were combined with chlorhexidine hydrate using methods similar to those described in Examples 1 and 2. However, these polymers and the antimicrobial bisguanide compound did not form the molecular distribution due to a lack of molecular interaction between the two components. As a result, clumps of the bisguandide compound were formed. Thus, the blended product was not a miscible blend.

Example 4: Formation of Particulate Forms of the Antimicrobial Material

Antimicrobial polymeric materials were prepared using a commercial extruder (Wernes Phleidere Twin Screw Extruder ZSK 30, D=30 mm, L/D=5) with an automatic feeder for resin (K-Tron single-screw, Model K2U-T35) and a separate feeder for chlorhexidine (K=Tron feed, single screw) to obtain a strand of extrudate from the die. The extruder included six temperature zones, with the zone nearest the hopper having a temperature of approximately 100° C. and the remaining five temperature zones having temperatures of about 150° C.

The thermoplastic polymer was the same low density polyethylene (LDPE) as set forth in Example 1. The chlorhexidine was fed into the extruder in an amount sufficient to provide 5% by weight of the extruded resin. The strand of extrudate was chopped to provide an average diameter of 80 mesh pellets.

Example 5: Preparation of a Polyolefin Elastomer Blend

Figure 11A:
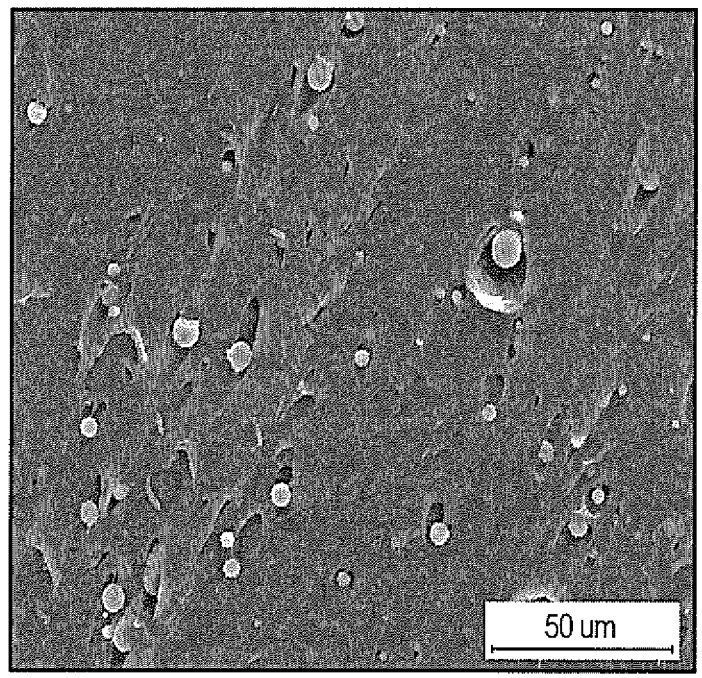
FIGS. 11A and 11B are SEM images of a mixture of chlorhexidine and resin.
Figure 11B:
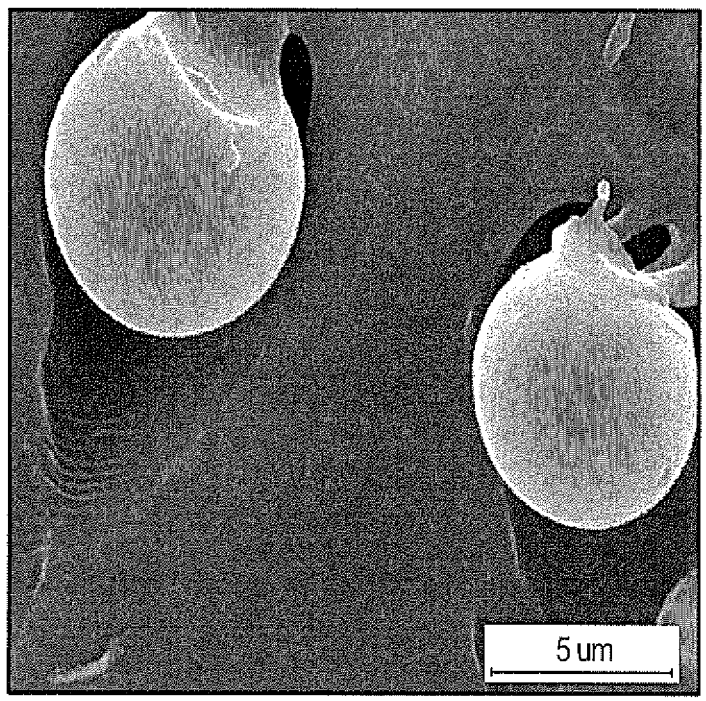

To avoid the thermal decomposition of the chlorhexidine hydrate, a lower temperature polyolefin elastomer type resin (DOW Engage™ 8411) was used to prepare pellets in a commercial extruder. The chlorhexidine hydrate was fed into the extruder described in Example 4 in an amount sufficient to provide 10% by weight of the extruded pellet. The pellets were pulverized cryogenically (liquid nitrogen) to provide an average of 20 mesh particles. Although the chlorhexidine hydrate melted, it did not solubilize within the resin to form a miscible blend. The SEM micrographs (FIGS. 11A and 11B) of the resulting resin illustrate the failure of the chlorhexidine to form a solid solution with the resin.

Example 6: Antimicrobial Testing

The polymer blends prepared in Examples 1, 4, and 5 hereinabove were pulverized to obtain from 325 to 20 mesh particle sizes and tested for antimicrobial activity using colonized $E.\ coli$ dispersions. The particles were packed in a 12.0 in×1.0 in diameter acrylic tube to obtain a particle bed thickness of 0.5 in, 1.0 in, 1.5 in, or 2.0 in. A liquid culture of $E.\ coli$ ($10^8$ CFU concentration) was allowed to flow through the packed tube under gravity flow and at STP conditions. Although the flow rate was barely a steady stream, it was sufficient to evaluate the antimicrobial activity of the polymer blends.

Bacterial recovery was determined by Aerobic Plate Count and is shown in Table 3. The total reduction in bacterial growth was obtained by subtracting the log of the number of colony forming units per mL (CFU/mL) of the effluent samples by the log of the number of CFU/mL of the control.

TABLE 3

Reduction of Bacterial Growth Using Antimicrobial Polymeric Materials

| Purification Material (Thickness, in) | Initial Bacteria (CFU/mL) | Log | Effluent Bacteria (CFU/mL) | Log | Reduction in Bacteria |
|---|---|---|---|---|---|
| Chlorhexidine (5%)-LDPE (Lab-Scale -- 1.0 in) | $237 \times 10^8$ | 10.37 | $25 \times 10^3$ | 4.40 | 5.98 |
| Chlorhexidine (5%)-LDPE (Extruder -- 0.5 in) | $-9 \times 10^9$ | 9.95 | $1 \times 10^2$ | 2.00 | 7.95 |
| Chlorhexidine (5%)-LDPE (Extruder -- 1.0 in) | $-9 \times 10^9$ | 9.95 | $3.7 \times 10^3$ | 3.57 | 6.38 |
| Chlorhexidine (5%)-LDPE (Extruder -- 2.0 in) | $-9 \times 10^9$ | 9.95 | $1 \times 10^2$ | 2.00 | 7.95 |
| Chlorhexidine (10%)-Engage (Extruder -- 1.0 in) | $1.07 \times 10^7$ | 7.03 | $1 \times 10^1$ | 1.00 | 6.03 |
| Chlorhexidine (10%)-Engage (Extruder -- 1.5 in) | $1.07 \times 10^7$ | 7.03 | $3 \times 10^1$ | 1.48 | 5.55 |
| Chlorhexidine (10%)-Engage (Extruder -- 2.0 in) | $1.07 \times 10^7$ | 7.03 | $3 \times 10^1$ | 1.48 | 5.55 |

There was an approximately Log-6 to Log-8 reduction of the $E.\ coli$ which was passed through the packed tubes of the chlorhexidine-low density polyethylene alloys, whereas there was only a Log-5.5 reduction of the $E.\ coli$ was observed with the packed tubes of the chlorhexidine-Engage™ alloys at a higher concentration of the chlorhexidine. Not wishing to be bound by any theory, it is believed that the enhanced antimicrobial activity may be attributed to the immobilization of the antimicrobial bisguanide compound as a molecular blend within the polymer.

Figure 12A:
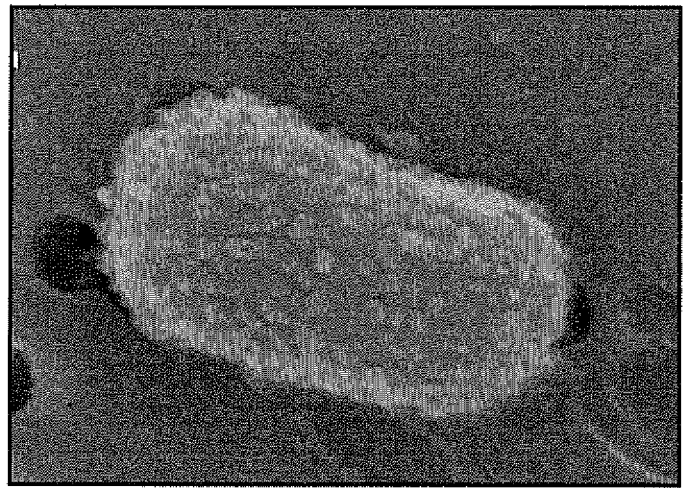
FIGS. 12A and 12B are SEM images of *E. coli* cells exposed to an antimicrobial polymer material according to an embodiment.
Figure 12B:
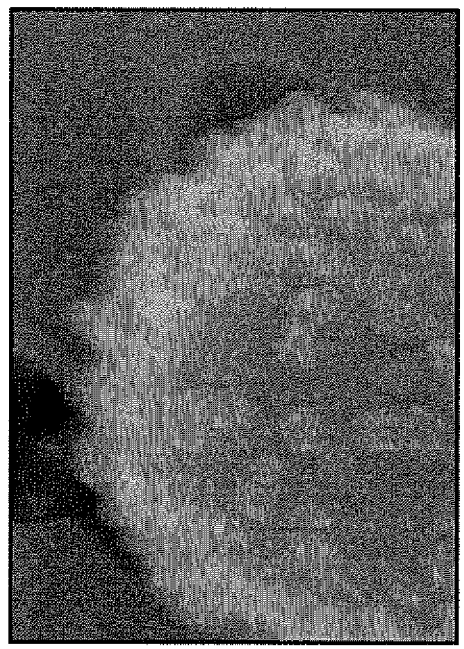

An SEM micrograph of a dead $E.\ coli$ cell, shown in FIGS. 12A and 12B, illustrates the surface-dependent mechanism of the antimicrobial polymer material's antimicrobial activity. The sites of collision with the chlorhexidine in the polymer blend are visible and appear to have caused disassembly on the cell wall. Not wishing to be bound by any theory, it is believed that the cell wall was pulled apart upon collision via Brownian motion with the surfaces of the antimicrobial polymer blend. The cell wall is further magnified in FIG. 12B, where the frayed fibrous cell wall material can be observed.

Figure 13:
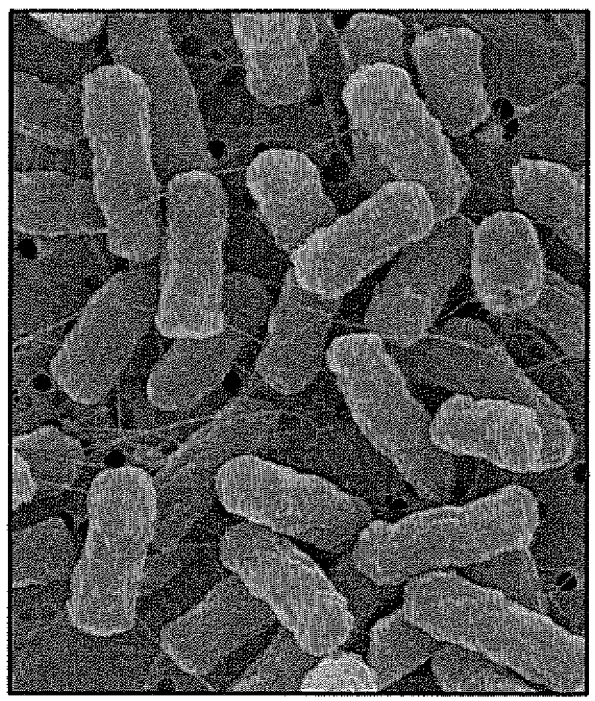
FIG. 13 is an SEM image of *E. coli* cells exposed to conventional antimicrobial materials.

Generally, a typical dead $E.\ coli$ cell (FIG. 13) does not show any change in its surface morphology except for possible shrinkage due to loss of cytoplasm. This mechanism of activity generally is attributed to a soluble oxidant or surface active agent, such as a soluble chlorhexidine salt, that undergoes a second order chemical reaction (i.e., the agent is consumed in a stoichiometric type relationship). The antimicrobial polymer blend, conversely, appears to react catalytically with the microorganisms and is not consumed during the reaction.

Example 7: Analysis of Leaching

The effluent water stream from Example 6 also was tested by a standard HPLC method to evaluate the amount, if any, of the antimicrobial bisguanide that may have leached into the effluent water. Less than 2 ppm of the insoluble antimicrobial bisguanide compound was detected in the effluent of the low density polyethylene alloys produced on the lab scale while less than 1 ppm of the insoluble antimicrobial bisguanide compound was detected in the effluent of the low density polyethylene alloys produced on the production scale, indicating that substantially all of the insoluble antimicrobial bisguanide compound remained distributed within the polymer blend. Conversely, over 20 ppm of the insoluble antimicrobial bisguanide compound was detected in the effluent of the Engage™ blends, indicating that the antimicrobial bisguanide compound was not immobilized within the polymer.

Distilled water was flowed through the tubes after the foregoing experiments to determine whether there was a soluble portion of the insoluble antimicrobial bisguanide which was responsible for the observed antimicrobial activity which is common with soluble antimicrobial bisguanide salts (e.g., chlorhexidine gluconate). The results were negative for each of the low density polyethylene alloys.

Example 8: Preparation and Testing of Fibers

Extruded fibers were prepared from an antimicrobial polymeric material (1% chlorhexidine-99% polyethylene blend) ("1%" or "1% drawn fiber"). Bi-component fibers were prepared by co-extruding an antimicrobial polymeric material (5% chlorhexidine, 95% polyethylene) and polyethylene ("5%" or "5% bicomponent fiber"). The antimicrobial polymeric material comprised the outer sheath of the fibers and the polyethylene comprised the core of the fibers.

The fibers were inoculated with 1 mL of a bacterial solution of a 24-hour culture of Staphylococcus aureus ($8.58 \times 10^6$ CFU/mL, Log 6.93). After the fiber was exposed to the inoculant for a predetermined amount of time (1 minute, 5 minutes, 10 minutes, 30 minutes, 1 hour, 6 hours, and 24 hours), the fiber was mixed with a buffer solution, samples were diluted using serial dilutions, and plated, according to Standard Methods 9215B. Plates were incubated for 48 hours+/−2 hours at 35±0.5° C. Plates were then counted for total number of colonies present (CFU/mL) and the log reduction was calculated by subtracting the sample log from the initial culture log (Culture log−Sample log=reduction of bacteria log). The results are summarized in the following table, where A and B represent the 1% drawn fiber and C and D represent the 5% bicomponent fiber.

| Grab Sample ID | Fiber Type | Inoculant Time (min) | CFU/mL S. aureus Count | Log of CFU/mL | Log Reduction |
|---|---|---|---|---|---|
| 1-1A | 1% | 1 | 40 | 1.60 | 5.33 |
| 2-1B | 1% | 1 | 32 | 1.51 | 5.42 |
| 3-1C | 5% | 1 | 0 | — | 6.93 |
| 4-1D | 5% | 1 | 0 | — | 6.93 |
| 5-2A | 1% | 5 | 22 | 1.34 | 5.59 |
| 6-2B | 1% | 5 | 29 | 1.46 | 5.47 |
| 7-2C | 5% | 5 | 0 | — | 6.93 |
| 8-2D | 5% | 5 | 0 | — | 6.93 |
| 9-3A | 1% | 10 | 30 | 1.48 | 5.45 |
| 10-3B | 1% | 10 | 20 | 1.30 | 5.63 |
| 11-3C | 5% | 10 | 0 | — | 6.93 |
| 12-3D | 5% | 10 | 0 | — | 6.93 |
| 13-4A | 1% | 30 | 12 | 1.08 | 5.85 |
| 14-4B | 1% | 30 | 9 | 0.95 | 5.98 |
| 15-4C | 5% | 30 | 0 | — | 6.93 |
| 16-4D | 5% | 30 | 0 | — | 6.93 |
| 17-5A | 1% | 60 (1 hr) | 1 | 0 | 6.93 |
| 18-5B | 1% | 60 (1 hr) | 2 | 0.30 | 6.63 |
| 19-5C | 5% | 60 (1 hr) | 0 | — | 6.93 |
| 20-5D | 5% | 60 (1 hr) | 0 | — | 6.93 |
| 21-6A | 1% | 360 (6 hr) | 1 | 0 | 6.93 |
| 22-6B | 1% | 360 (6 hr) | 0 | — | 6.93 |
| 23-6C | 5% | 360 (6 hr) | 0 | — | 6.93 |
| 24-6D | 5% | 360 (6 hr) | 0 | — | 6.93 |
| 25-7A | 1% | 1440 (24 hr) | 0 | — | 6.93 |
| 26-7B | 1% | 1440 (24 hr) | 0 | — | 6.93 |
| 27-7C | 5% | 1440 (24 hr) | 0 | — | 6.93 |
| 28-7D | 5% | 1440 (24 hr) | 0 | — | 6.93 |

Example 9: Preparation and Testing of Fibers

Extruded fibers were prepared from an antimicrobial polymeric material (1% chlorhexidine-99% polyethylene blend) ("1%" or "1% drawn fiber"). Bi-component fibers were prepared by co-extruding an antimicrobial polymeric material (5% chlorhexidine, 95% polyethylene) and polyethylene ("5%" or "5% bicomponent fiber"). The antimicrobial polymeric material comprised the outer sheath of the fibers and the polyethylene comprised the core of the fibers.

The fibers were inoculated with 1 mL of a bacterial solution of a 24-hour culture of Methicillin-resistant Staphylococcus aureus (6.55×10⁷ CFU/mL, Log 7.82). After the fiber was exposed to the inoculate for a predetermined amount of time (1 minute, 5 minutes, 10 minutes, 30 minutes, 1 hour, 6 hours, and 24 hours), the fiber was mixed with a buffer solution, samples were diluted using serial dilutions, and plated, according to Standard Methods 9215B. Plates were incubated for 48 hours+/−2 hours at 35±0.5° C. Plates were then counted for total number of colonies present (CFU/mL) and the log reduction was calculated by subtracting the sample log from the initial culture log (Culture log−Sample log=reduction of bacteria log). The results are summarized in the following table, where A and B represent the 1% drawn fiber and C and D represent the 5% bicomponent fiber.

| Grab Sample ID | Fiber Type | Inoculant Time (min) | CFU/mL S. aureus Count | Log of LCFU/mL | Log Reduction |
|---|---|---|---|---|---|
| 1-1A | 1% | 1 | 2400 | 3.38 | 4.44 |
| 2-1B | 1% | 1 | 2340 | 3.37 | 4.45 |
| 3-1C | 5% | 1 | 292 | 2.47 | 5.35 |
| 4-1D | 5% | 1 | 286 | 2.46 | 5.36 |
| 5-2A | 1% | 5 | 2800 | 3.45 | 4.37 |
| 6-2B | 1% | 5 | 2600 | 3.41 | 4.41 |
| 7-2C | 5% | 5 | 18 | 1.26 | 6.56 |
| 8-2D | 5% | 5 | 24 | 1.38 | 6.44 |
| 9-3A | 1% | 10 | 1600 | 3.20 | 4.62 |
| 10-3B | 1% | 10 | 1700 | 3.23 | 4.59 |
| 11-3C | 5% | 10 | 2 | 0.30 | 7.52 |
| 12-3D | 5% | 10 | 7 | 0.84 | 6.98 |
| 13-4A | 1% | 30 | 150 | 2.18 | 5.64 |
| 14-4B | 1% | 30 | 140 | 2.15 | 5.67 |
| 15-4C | 5% | 30 | 0 | — | 7.82 |
| 16-4D | 5% | 30 | 4 | 0.60 | 7.22 |
| 17-5A | 1% | 60 (1 hr) | 32 | 1.51 | 6.31 |
| 18-5B | 1% | 60 (1 hr) | 24 | 1.38 | 6.44 |
| 19-5C | 5% | 60 (1 hr) | 0 | — | 7.82 |
| 20-5D | 5% | 60 (1 hr) | 0 | — | 7.82 |
| 21-6A | 1% | 360 (6 hr) | 0 | — | 7.82 |
| 22-6B | 1% | 360 (6 hr) | 0 | — | 7.82 |
| 23-6C | 5% | 360 (6 hr) | 0 | — | 7.82 |
| 24-6D | 5% | 360 (6 hr) | 0 | — | 7.82 |
| 25-7A | 1% | 1440 (24 hr) | missing | | |
| 26-7B | 1% | 1440 (24 hr) | missing | | |
| 27-7C | 5% | 1440 (24 hr) | missing | | |
| 28-7D | 5% | 1440 (24 hr) | missing | | |

Example 10: Preparation and Testing of Bi-Component Fibers

The foregoing experiment was repeated by inoculating the 5% bicomponent fiber with a mixture of 4 different types of bacteria, including E. coli, Enterobacter aerogenes, Pseudomonas aruginosa, and Streptococcus pyogenses (a minimum total bacterial concentration of 6.34 log) to evaluate the effectiveness of the fibers on both gram-positive and gram-negative bacteria. After the fiber was exposed to the inoculate for a predetermined amount of time (1 minute, 5 minutes, 10 minutes, 30 minutes, 1 hour, 6 hours, and 24 hours), the fiber was mixed with a buffer solution (100 mL), shaken, and the contents of the buffer solution were plated. Plates were incubated for 48 hours at 35±0.5° C. Plates were then counted for total number of colonies present (CFU/mL) and the log reduction was calculated by subtracting the sample log from the initial culture log (Culture log−Sample log=reduction of bacteria log). The results are summarized in the following table, where A and B represent separate samples of the 5% bicomponent fiber.

| Grab Sample ID | Time (min.) | CFU/mL | Log of CFU/mL | Log Reduction | Average Log Reduction |
|---|---|---|---|---|---|
| 1-1A | 1 | 850 | 2.93 | 3.41 | 3.375 |
| 2-1B | 1 | 1000 | 3 | 3.34 | |
| 5-2A | 5 | 310 | 2.49 | 3.85 | 3.865 |
| 6-2B | 5 | 290 | 2.46 | 3.88 | |
| 9-3A | 10 | 27 | 1.43 | 4.91 | 4.885 |
| 10-3B | 10 | 30 | 1.48 | 4.86 | |
| 13-4A | 30 | 3 | 0.48 | 5.86 | 5.95 |
| 14-4B | 30 | 2 | 0.3 | 6.04 | |
| 17-5A | 60 (1 hr.) | 1 | 0 | 6.34 | 6.1 |
| 18-5B | 60 (1 hr.) | 3 | 0.48 | 5.86 | |
| 21-6A | 360 (6 hr.) | 0 | — | 6.34 | 6.34 |
| 22-6B | 360 (6 hr.) | 0 | — | 6.34 | |

-continued

| Grab Sample ID | Time (min.) | CFU/mL | Log of CFU/mL | Log Reduction | Average Log Reduction |
|---|---|---|---|---|---|
| 25-7A | 1440 (24 hr.) | 0 | — | 6.34 | 6.34 |
| 26-7B | 1440 (24 hr.) | 0 | — | 6.34 | |

The foregoing data was very similar to the data observed in Example 9, where at each subsequent time period there was a higher reduction of bacteria. The 5% bicomponent fibers took 10 minutes to achieve greater then a 99.99% reduction of the mixture of bacteria, 30 minutes to achieve a greater than 99.9999% reduction of bacteria, and 6 hours to achieve the target of 100% reduction in bacteria.

Publications cited herein and the materials for which they are cited are specifically incorporated herein by reference. Modifications and variations of the methods and devices described herein will be obvious to those skilled in the art from the foregoing detailed description. Such modifications and variations are intended to come within the scope of the appended claims.

What is claimed is:

1. An antimicrobial fibrous material comprising a solid miscible blend of chlorhexidine and at least one polyethylene polymer with a melting temperature less than about 165° C., wherein the at least one polyethylene polymer and the chlorhexidine are melted and blended together, and the solid miscible blend is from about 5% to about 10% by weight chlorhexidine and the chlorhexidine is distributed at the molecular level within the at least one polyethylene polymer and immobilized within the solid miscible blend.

2. The antimicrobial fibrous material of claim 1, wherein the solid miscible blend is substantially free of degraded chlorhexidine.

3. The antimicrobial fibrous material of claim 1, wherein the at least one polyethylene polymer has a melting temperature of less than 135° C.

4. The antimicrobial fibrous material of claim 1, wherein the miscible blend is about 5% by weight chlorhexidine.

5. The antimicrobial fibrous material of claim 1, wherein the antimicrobial fibrous material is porous.

6. The antimicrobial fibrous material of claim 1, wherein the antimicrobial fibrous material forms at least one layer in a barrier structure that is spray impact and fluid penetration resistant.

7. A protective article comprising the barrier structure of claim 6, wherein the protective article is a garment, a surgical drape, a surgical fenestration cover, a sheet, a linen, a padding, a gauze dressing, a wipe cloth, or a sponge.

8. The protective article of claim 7, wherein the garment is a gown, a robe, a face mask, a head cover, a shoe cover, or a glove.

9. The protective article of claim 7, wherein the garment is a face mask.

10. The protective article of claim 7, wherein the barrier structure is a gauze dressing.

11. The antimicrobial fibrous material of claim 1, wherein the antimicrobial fibrous material is in a non-woven form.

* * * * *